United States Patent
Bloch et al.

(10) Patent No.: US 10,632,305 B2
(45) Date of Patent: Apr. 28, 2020

(54) METHODS OF GENERATING MATURE HUMAN MUSCLE FIBERS

(71) Applicant: The University of Maryland, Baltimore, Baltimore, MD (US)

(72) Inventors: Robert J. Bloch, Baltimore, MD (US); Andrea O'Neill, Towson, MD (US); Joseph A. Roche, Balitmore, MD (US); Paraskevi Sakellariou, Athens (GR)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 783 days.

(21) Appl. No.: 15/029,191

(22) PCT Filed: Oct. 17, 2014

(86) PCT No.: PCT/US2014/061262
§ 371 (c)(1),
(2) Date: Apr. 13, 2016

(87) PCT Pub. No.: WO2015/058161
PCT Pub. Date: Apr. 23, 2015

(65) Prior Publication Data
US 2016/0256681 A1    Sep. 8, 2016

Related U.S. Application Data

(60) Provisional application No. 61/892,104, filed on Oct. 17, 2013.

(51) Int. Cl.
*A61N 1/32* (2006.01)
*A61K 35/34* (2015.01)
(Continued)

(52) U.S. Cl.
CPC .......... *A61N 1/326* (2013.01); *A01K 67/0271* (2013.01); *A61F 2/08* (2013.01);
(Continued)

(58) Field of Classification Search
CPC ................ A61N 1/326; A61N 1/36003; A01K 67/0271; A01K 2207/12; A01K 2227/105;
(Continued)

(56) References Cited

U.S. PATENT DOCUMENTS 5,833,978 A    11/1998  Tremblay
7,582,417 B2   9/2009   Wehrman et al.
(Continued)

FOREIGN PATENT DOCUMENTS

WO         01-19379 A2    3/2001

OTHER PUBLICATIONS

International Search Report and Written Opinion for the corresponding PCT Application # PCT/US2014/061262, dated Jan. 27, 2015, pp. 1-17.
(Continued)

*Primary Examiner* — Lauren P Farrar
(74) *Attorney, Agent, or Firm* — Beusse Wolter Sanks & Maire; Eugene J. Molinelli

(57) ABSTRACT

Studies of the pathogenic mechanisms underlying human myopathies and muscular dystrophies often require animal models, but models of some human diseases are not yet available. The present invention provides methods to promote the engraftment and development of myogenic cells from individuals with such diseases into mature muscle tissue in mice to treat muscle diseases, muscle injury and reduced muscle function. Immortalized human myogenic precursor cells (hMPCs) form mature human myofibers following implantation into the hindlimbs of immunodeficient mice. The engraftment of the cells and their development into mature muscle myofibers is promoted by intermittent neuromuscular electrical stimulation (iNMES) of the peroneal nerve of the engrafted limb. The human myofibers that form are innervated, their contractile apparatus is fully (Continued)

differentiated, and they are comprised of human myonuclei, with minimal contamination by murine myonuclei.

18 Claims, 11 Drawing Sheets

(51) Int. Cl.
*A01K 67/027* (2006.01)
*A61F 2/08* (2006.01)
*A61N 1/36* (2006.01)

(52) U.S. Cl.
CPC .......... *A61K 35/34* (2013.01); *A61N 1/36003* (2013.01); *A01K 2207/12* (2013.01); *A01K 2227/105* (2013.01); *A01K 2267/035* (2013.01); *A61F 2002/0894* (2013.01)

(58) Field of Classification Search
CPC ................ A01K 2267/035; A61F 2/08; A61F 2002/0894; A61K 35/34
See application file for complete search history.

(56) References Cited

U.S. PATENT DOCUMENTS

| | | | |
|---|---|---|---|
| 2007/0177536 A1* | 8/2007 | Brueck | H04W 72/1268 370/328 |
| 2011/0113496 A1* | 5/2011 | Shultz | A01K 67/0278 800/11 |
| 2012/0177577 A1* | 7/2012 | Ostertag | A01K 67/0276 424/9.2 |
| 2012/0213744 A1* | 8/2012 | Rudnicki | A61K 38/1709 424/93.7 |

OTHER PUBLICATIONS

Distefano, G., et al., "Neuromuscular Electrical Stimulation as a Method to Maximize the Beneficial Effects of Muscle Stem Cells Transplanted into Dystrophic Skeletal Muscle," PLOS One, Mar. 2013, pp. 1-11, vol. 8, Issue 3.
Vilquin, J., et al., "Normal growth and regenerating ability of myoblasts from unaffected muscles of facioscapulohumeral muscular dystrophy patients," Gene Therapy, 2005, pp. 1651-1662, vol. 12, No. 22, Publisher: Nature Publishing Group.
Pye, et al., "Identification of the RAG-1 as a suitable mouse model for mitochondrial DNA disease", Neuromuscular Disorders, May 1, 2004, pp. 329-336, vol. 14, No. 5.
Ma, et al., "Clone-derived human AF-amniotic fluid stem cells are capable of skeletal myogenic differentiation in vitro and in vivo", Journal of Tissue Engineering and Regenerative Medicine, Aug. 7, 2012, pp. 598-613, vol. 6, No. 8.
Fabrisia Ambrosio et al: "The Synergistic Effect of Treadmill Running on Stem-Cell Transplantation to Heal Injured Skeletal Muscle", Tissue Engineering Part A, 2010, pp. 839-849, vol. 16, No. 3.
Extended European Search Report, EP Application No. 14853877.0, dated Mar. 22, 2017, pp. 1-11.
Ambrosio, F., et al., "A murine model of muscle training by neuromuscular electrical stimulation," J. Vis. Exp., 2012, pp. 1-6, Issue: 63.
Bouchentouf, M., et al., "Exercise improves the success of myoblast transplantation in mdx mice," Neuromuscul. Disord., 2006, pp. 518-529, vol. 16.
Dirks, M.L., et al., Neuromuscular electrical stimulation prevents muscle disuse atrophy during leg immobilization in humans, Acta. Physiol. (Oxf), 2014, pp. 628-641, vol. 210.
Distefano, G., et al., "Neuromuscular electrical stimulation as a method to maximize the beneficial effects of muscle stem cells transplanted into dystrophic skeletal muscle," PLoS One, 2013, pp. 1-11, vol. 8.
Ehrhardt, J., et al., "Human muscle precursor cells give rise to functional satellite cells in vivo," Neuromuscul. Disord., 2007, pp. 631-638, vol. 17.
Fakhfakh, R., et al., "Administration of a soluble activin type IIB receptor promotes the transplantation of human myoblasts in dystrophic mice," Cell Transplant, 2012, pp. 1419-1430, vol. 21.
Lovering, R.M., et al., "Recovery of function in skeletal muscle following 2 different contraction-induced injuries," Arch. Phys. Med. Rehabil., 2007, pp. 617-625, vol. 88.
Mamchaoui, K, et al., "Immortalized pathological human myoblasts: towards a universal tool for the study of neuromuscular disorders," Skeletal Muscle, 2011, pp. 11, vol. 1.
McLoughlin, T.J., et al., "Sensory level electrical muscle stimulation: effect on markers of muscle injury," Br. J. Sports Med., 2004, pp. 725-729, vol. 38.
Pedrotty, D.M., et al., "Engineering skeletal myoblasts: roles of three-dimensional culture and electrical stimulation," Am. J. Physiol Heart Circ. Physiol, 2005, pp. 1620-1626, vol. 288.
Quattrocelli, M., et al., "Cell therapy strategies and improvements for muscular dystrophy," Cell Death Differ., 2010, pp. 1222-1229, vol. 17.
Riederer, I., et al., "Slowing down differentiation of engrafted human myoblasts into immunodeficient mice correlates with increased proliferation and migration," Mol. Ther., 2012, pp. 146-154, vol. 20.
Roche, J.A., et al., "Extensive mononuclear infiltration and myogenesis characterize recovery of dysferlin-null skeletal muscle from contraction-induced injuries," Am. J. Physiol Cell Physiol, 2010, pp. C298-312, vol. 298.
Serena, E., et al., "Electrophysiologic stimulation improves myogenic potential of muscle precursor cells grown in a 3D collagen scaffold," Neurol. Res., 2013, pp. 207-214, vol. 30.
Silva-Barbosa, S.D., et al., "Comparative analysis of genetically engineered immunodeficient mouse strains as recipients for human myoblast transplantation," Cell Transplant, 2005, pp. 457-467, vol. 14.
Stern-Straeter, J., et al., "Impact of electrical stimulation on three-dimensional myoblast cultures—a real-time RT-PCR study," J. Cell Mol. Med., 2005, pp. 883-892, vol. 9.
Wang, W.J., et al., "Electrical stimulation promotes motor nerve regeneration selectivity regardless of end-organ connection," J. Neurotrauma, 2009, pp. 641-649, vol. 26.
Zhang, Y., et al., "Human skeletal muscle xenograft as a new preclinical model for muscle disorders," Hum. Mol. Genet, 2014, pp. 3180-3188, vol. 23.
Zhou, D., et al., "Developmental expression of spectrins in rat skeletal muscle," Mol. Biol. Cell, 1998, pp. 47-61, vol. 9.

* cited by examiner

METHODS OF GENERATING MATURE HUMAN MUSCLE FIBERS

CROSS-REFERENCE TO RELATED APPLICATIONS

This application is a 371 national stage application of PCT Application No. PCT/US2014/061262, filed Oct. 17, 2014, and claims the benefit of Provisional application 61/892,104, filed Oct. 17, 2013, under 35 U.S.C. § 119(e), the entire contents of each application are hereby incorporated by reference as if fully set forth herein.

STATEMENT OF GOVERNMENTAL INTEREST

This invention was made with government support under Grant No. HD060848 awarded by the National Institutes of Health. The government has certain rights in the invention.

BACKGROUND

Muscular dystrophies afflict approximately 1 in 5000 individuals worldwide. The development of animal models to study these diseases is essential in understanding the mechanisms of pathogenesis and to test potential therapies for people afflicted with these diseases. Animal models for some muscular dystrophies, such as facioscapulohumeral muscular dystrophy ("FSHD") and oculopharyngeal muscular dystrophy ("OPMD"), are still unavailable. Furthermore, some murine models of some muscular dystrophies, whether naturally occurring or genetically engineered, are limited because they do not replicate all the features of the human disease.

An animal model that carries human muscles from individuals with these diseases would serve as a more accurate model, reproducing most, if not all, of the morphological, physiological and genomic features of the muscular dystrophies in man. The present invention describes methods to develop such a model, while solving the problem of the presence of murine myonuclei in the graft. Here, intermittent neuromuscular electrical stimulation (iNMES) is applied to immunodeficient mice engrafted with an immortalized clonal cell line of human myogenic precursor cells ("hMPCs") that express luciferase ("LHCN" cells).

Previous studies of grafts of hMPCs create hybrid fibers, containing myonuclei of both human and murine origin form, and the fibers express proteins found both in man and in mice. In the present invention, muscle of the host mouse was eliminated by injection of a myotoxin and the myogenic potential of any remaining tissue was suppressed by X-irradiation. Human myogenic precursor cells were then injected. The survival and differentiation of the human muscle tissue were promoted with electrical stimulation. Many of the myofibers in that graft were similar to nearby murine myofibers in size, and they were both innervated by motor neurons and fully differentiated. More importantly, they were comprised almost exclusively of human myonuclei, with minimal contamination by murine myonuclei.

SUMMARY

It has been discovered that muscle formed from transplanted LHCN cells is highly differentiated and innervated, and is composed of myofibers of human origin, with minimal contamination by murine myonuclei. It has also been discovered that neuromuscular electrical stimulation ("NMES") enhances engraftment of these immortalized human myoblasts in animals.

In certain embodiments, methods are provided for treating a subject having a muscle disorder. First, a subject having the muscle disorder is identified. Human myogenic precursor cells in an amount capable of forming mature muscle tissue are injected into a portion of a limb of the subject. A nerve of the limb is then subjected to a regime of therapeutic stimulation (e.g., NMES) configured to promote and enhance engraftment of the human myogenic precursor cells. A graft is created and promotes formation of mature muscle tissue that improves the function of muscle. In some embodiments, the subject is a non-human mammal, e.g., a mouse. If the subject is non-human, it must be immunodeficient, and thus incapable of mounting an immune response to injected human cells and the subsequent graft.

In some aspects, the invention further provides a method for producing a non-human animal that models a human muscular disease. A non-human animal such as an immunocompromised mouse suitable for xenografting is obtained. The limb (e.g., a hindlimb) of the non-human animal is irradiated by exposure to with X-rays or other form of irradiation known in the art. Muscle (i.e., the Tibialis anterior muscle "TA") of that limb was then injected along its length with a toxin such as cardiotoxin, a phospholipase that causes the muscle to degenerate. hMPCs capable of forming muscle tissue were injected into the compartment formerly occupied by the degenerated muscle tissue and then the peroneal nerve serving that compartment was subjected to electrical stimulation to enhance engraftment of the myoblast cells so that they develop into mature muscle tissue. The engraftment of the myogenic precursor cells in the limb treated with a regime of electrical stimulation, such as NMES, was improved compared to engraftment of a population of untreated myoblast cells. The myogenic precursor cells can be derived from healthy humans or from individuals with certain muscle diseases, notably Facioscapulohumeral Muscular Dystrophy (FSH or FSHD). Non-human animal models generated by this method in animals other than mice are also contemplated.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
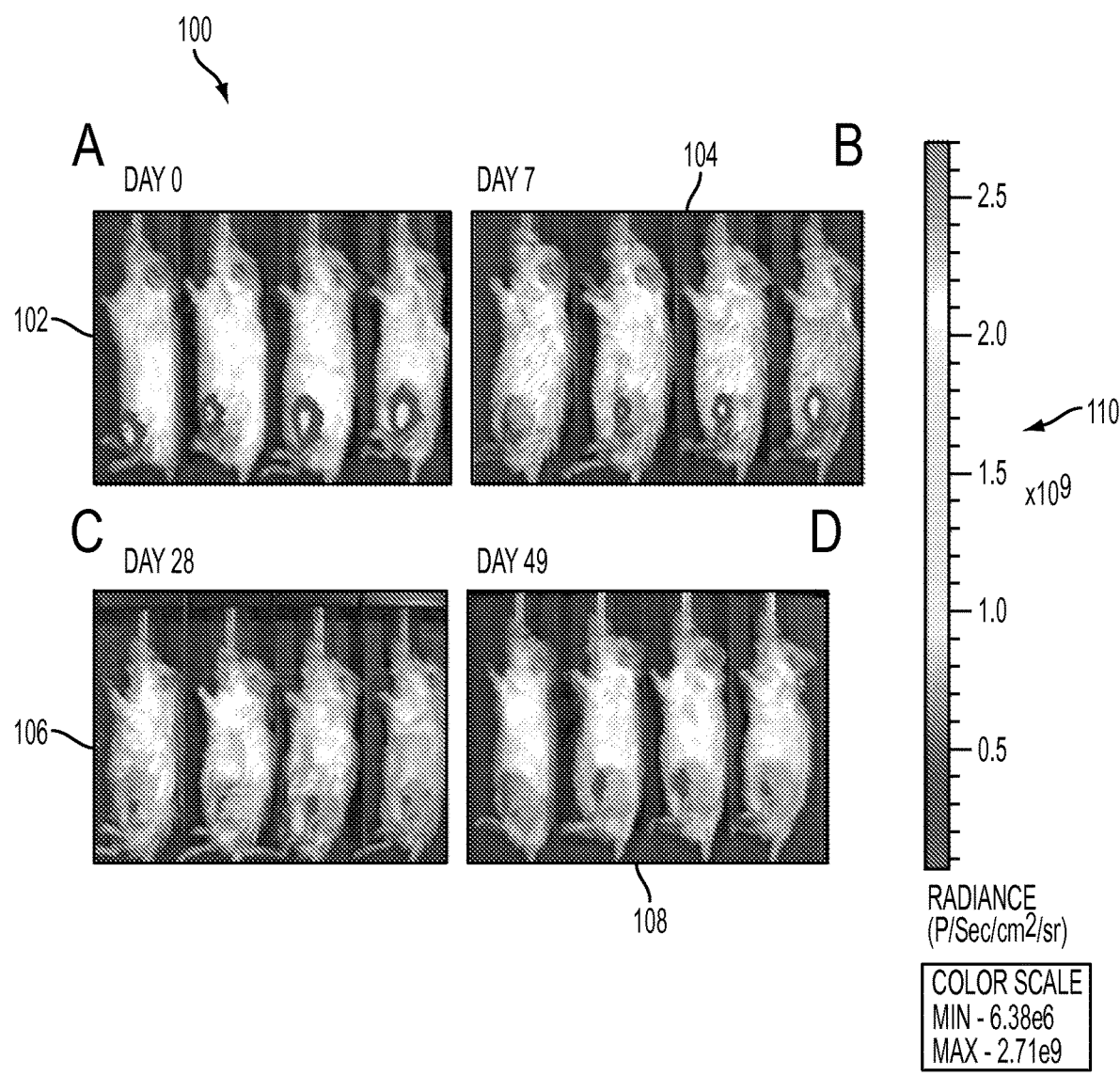
FIG. 1A-1D are representative BLI images of NOD-RAG mice on days 0, 7, 28, and 49 after injection with $5\times10^6$ or with $2\times10^6$ LHCN cells and subjected to 4 weeks of NMES, according to an embodiment.

One or more methods are described for (i) enhancing engraftment of myogenic precursor cells; (ii) generating mature muscle fibers; (iii) treating muscle disorders and (iv) producing non-human animals that model muscle disease e.g., FSHD. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. Various references are cited in the following. The entire contents of the following references are hereby incorporated by reference as if fully set forth herein, except for terminology that is inconsistent with the terminology used herein.

Some embodiments of the invention are described below in the context of a mouse model that has a muscle disease. However, the invention is not limited to this context. In other embodiments the subject is a human being or other animal.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The following terms as used herein have the corresponding meanings given here.

1. DEFINITIONS

As used in this specification and the appended claims, the singular forms "a," "an," and "the" encompass embodiments having plural referents, unless the content clearly dictates otherwise. As used in this specification and the appended claims, the terms "or" is generally employed in its sense including "and/or" unless the content clearly dictates otherwise.

As used herein, the terms "animal," "patient," or "subject," mean any animal (e.g., mammals, including but not limited to humans, primates, dogs, cattle, cows, horses, kangaroos, pigs, sheep, goats, cats, rabbits, rodents, and transgenic non-human animals) that is to be the recipient of a particular treatment. Typically, the terms "animal," "subject," and "patient" are used interchangeably herein in reference to a human subject or a rodent. The preferred animal, patient, or subject is a human or a non-human mammal such as a mouse.

As used herein, the term "muscle disorder" is intended to broadly encompass muscle disease, muscle injuries, and muscle disorders, and defects that can impair and reduce muscle function including but not limited to physical injuries, burns, surgical tissue excisions, muscle wasting, muscular dystrophy, infarcts, ischemic events, neuromuscular disorders and muscle diseases including, but not limited to those, set forth in Table 1.

As used herein, "muscle cells" include, but are not limited to, skeletal muscle fibers, myofibers or myocytes, and may be of any suitable species, and in some embodiments are of the same species as the subject into which tissues are implanted. Mammalian cells (including mouse, rat, dog, cat, monkey and human cells) are in some embodiments particularly preferred.

As used herein, the term "muscle fiber" or "myofiber" refers to a multinucleated single muscle cell. Physically, e.g., in humans, they are highly elongated and are typically 50-100 microns in diameter, but range in length from a few millimeters many centimeters. Muscle fiber cells are formed from the fusion of myoblasts (a type of progenitor cell that gives rise to a muscle cell during development or, in adults, during regeneration following injury). The myofibers are long, cylindrical, multinucleated cells composed of actin and myosin myofibrils repeated as a sarcomere, the basic functional unit of the muscle fiber and responsible for skeletal muscle's striated appearance and forming the basic machinery necessary for muscle contraction.

As used herein, the term "myoblasts" are a type of muscle precursor cell. They are present in developing muscle and appear in adult muscle when satellite cells, muscle stem cells that are closely associated with myofibers in vertebrates, become activated. If the myofiber is injured, the myoblasts are capable of dividing and fusing to form a new myofiber. Typically, after muscle injuries, myofibers become necrotic and are removed by macrophages. This induces activation of stem cells and the proliferation and fusion of myoblasts to form multinucleated and elongated myotubes, which develop further into myofibers. The myofibers so generated form a more organized structure, namely muscle.

As used herein, the term "myocytes" are muscle cells, muscle fibers, or skeletal muscle cells, in either the mature or immature state.

As used herein, the term, "myofibrils" are the slender threads of a muscle fiber composed of numerous myofilaments. Myofibrils run from one end of the cell to the other and attach to the cell surface membrane at each end.

As used herein, the term "myotubes" are elongated, multinucleated cells, normally formed by the fusion of myoblasts. Myotubes have centrally located nuclei and myofibrils that tend to be poorly organized. In vertebrates, they develop into mature muscle fibers, which have peripherally-located nuclei and myofibrils that are well organized (e.g., in mammals). Under low serum conditions, myoblasts exit the cells cycle and fuse to form multinucleated myotubes, which become contractile.

As used herein, the term "xenograft" or "xenotransplant" refers to a transplanted cell, tissue, or organ derived from an animal of a different species. By way of an example, a graft from a mouse to a human is a xenograft.

As used herein, the term "xenotransplantation" refers to the process of transplantation of living cells, tissues or organs from one species to another, such as from mice to humans.

As used herein, the term "disease model" as used herein refers to the use of non-human animal models to obtain new information about human muscular diseases. In some embodiments, a population of cells from dystrophic patients, generated as the LHCN cells were generated, and injected into mice following the methods as disclosed herein, can be used in disease modeling experiments.

As used herein, the term "drug screening" as used herein refers to the use of cells and tissues in the laboratory to identify drugs with a specific function. In some embodiments, the present invention provides a subject for drug screening to identify compounds or drugs useful as therapies for diseases or illnesses (e.g. human muscle diseases or illnesses).

As used herein, the term "engrafting" or "engraftment" is used herein to refer to the ability of hMPCs or LHCN cells, provided by transplantation, to repopulate a tissue. The term encompasses all events surrounding or leading up to engraftment, such as tissue homing of cells, colonization of cells within the tissue of interest, and growth and differentiation of these cells into mature tissue. The engraftment efficiency or rate of engraftment can be evaluated or quantified using any experimentally acceptable parameter as known to those of skill in the art and can include cellular number and size. If the engrafted cells are engineered to express biologically active compounds, engraftment can also be quantified by the effects of these compounds, e.g., on the survival of the recipient. In one embodiment, engraftment is determined by measuring bioluminescence during a post-transplant period.

As used herein, the terms "subject" and "individual" are used interchangeably herein, and refer to an immunodeficient animal (e.g., either genetically or due to administration of irradiation such as X-rays or administration of immunosuppressive drugs), such as a mouse or human, to whom hMPCs or LHCN cells as disclosed herein can be implanted. The term "subject" also encompasses any vertebrate including but not limited to mammals, (e.g., humans, mice, rats), reptiles, amphibians and fish. However, advantageously, the subject is a mammal such as a mouse or human, or other mammal such as a domesticated mammal, e.g. dog, cat, horse, and the like, or production mammal, e.g. cow, sheep, pig, and the like are also encompassed in the term subject.

The terms "non-human animals" and "non-human mammals" are used interchangeably herein, and include mammals such as, mice, rats, rabbits, sheep, cats, dogs, cows, pigs, and non-human primates.

The term "tissue" refers to a group or layer of similarly specialized cells which together perform certain special functions. The term "tissue-specific" refers to a source or defining characteristic of cells from a specific tissue.

The terms, "enhance", "enhancing", and "enhanced" as used herein refer to activities whose effects are greater than that which is observed in a control or an untreated group or subject. Enhanced activity may be measured in vitro, in vivo, or in cell culture studies.

The terms "growth", "grow", "grown", or "growing" as used herein, mean the growth of tissue, including but not limited to one or more tissues, limbs or organs, following an injury of the tissue resulting from a diseases, disorder, trauma or other condition and includes but is not limited to regeneration as described herein below.

The terms "injury of a tissue" and "tissue injury" as used herein, mean damage of a tissue that disrupts its physical structure resulting in the impairment of its function.

The terms "injury of a limb" and "limb injury" as used herein, mean damage of a limb such as, for non-limiting examples, a finger, arm or foot, that involves a trauma to any or all of the tissues included in the limb.

As used herein, the terms "regenerate," "regenerating," or "regeneration" as used herein mean the restoration of a tissue, including but not limited to one or more tissues, limbs or organs, to its original state following an injury of the tissue resulting from a disease, disorder, trauma or other condition.

As used herein, the terms "stimulate", "stimulating", and "stimulated" refer to an activities whose effects are greater than that which is observed in a control or an untreated group. Stimulatory effects may be measured in vitro, in vivo or in cell culture studies.

As used herein, the term "therapeutic amount" or "therapeutically effective amount" means an amount that achieves the intended therapeutic effect of enhancing or stimulating regeneration of a tissue, including but not limited to one or more tissues, limbs or organs, in a subject. The full therapeutic effect does not necessarily occur by administration of one dose and may occur only after administration of a series of doses. Thus, a therapeutically effective amount may be administered in one or more administrations per day for successive days.

As used herein, the term "treating" means, means taking steps to obtain beneficial or desired results, including clinical results, such as alleviating or ameliorating one or more symptoms of a disease; diminishing the extent of disease; delaying or slowing disease progression; ameliorating and palliating or stabilizing a metric (statistic) of disease. "Treatment" refers to the steps taken.

2. OVERVIEW

Studies of the pathogenic mechanism underlying human myopathies and muscular dystrophies often require animal models, but models of some human diseases are not yet available, specifically for human diseases such as FSHD, the third most common form of muscular dystrophy in adults. Applicant discovered methods to promote the engraftment and development of myogenic cells from individuals with such diseases into mature muscle tissue in mice. Ultimately these methods and non-human models provide a useful tool for testing therapeutic drugs and other therapies.

Figure 11:
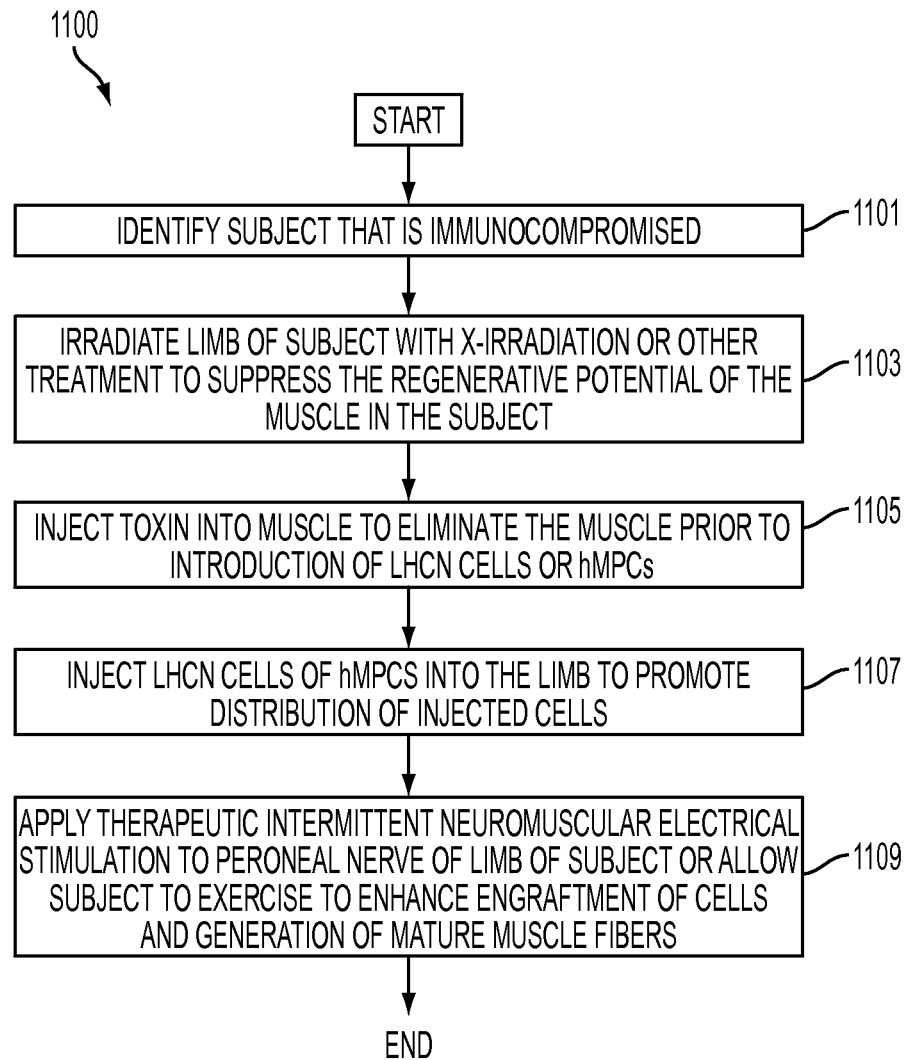
FIG. 11 is a flow chart that illustrates an example method for generating human muscle fibers, according to an embodiment.

FIG. 11 is a flow chart, 1100, that illustrates at a high level an example method for generating mature human muscle fibers in mice, according to an embodiment. Although steps are depicted in FIG. 11, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 1101, a subject is identified as immunocompromised and selected, such as a immunocompromised NRG 8-week-old mouse, suitable for xenografting because it cannot reject transplanted myogenic cells. NRG mice are also known as NOD-Rag immunodeficient mice or strain NOD.Cg-Rag1tm1MomIl2rgtm1Wjl/SzJ.

In step 1103, the left limb of the subject is subjected to a single, localized dose of X-irradiation or other treatment to suppress the regenerative potential of the muscle in the subject (i.e., drugs, genetic manipulation) which has been shown to suppress >90% of satellite cell activation. The radiation beam was focused on the lower hindlimb.

In step 1105, a toxin such as cardiotoxin (CTX), $BaCl_2$, or notexin was prepared and injected into three sites along the length of the muscle (e.g., TA muscle) to selectively induce degeneration of endogenous myofibers without affecting the blood vessels or muscle innervation.

In step 1107, LHCN cells, or hMPCs of different origins or hMPCs immortalized from satellite cells from a biopsy of the pectoralis major muscle of a 41-year-old male Caucasian heart-transplant donor, were further transduced with retrovirus to express luciferase constitutively. A single injection was performed into the muscle (e.g., TA compartment) along the bone, during which the needle was withdrawn slowly, to promote broad distribution of the injected cells. Bioluminescence imaging may be performed to monitor the survival and development of the grafted cells non-invasively by injecting a solution of D-luciferin IP into the subject and allowing it to distribute through the body. Imaging was performed.

In step 1109, intermittent neuromuscular electrical stimulation was performed to determine if it enhanced engraftment of the LHCN cells or hMPCs. The ankle dorsiflexors of the subject (i.e., mice) were stimulated by electrical stimulation through the intact skin over the common peroneal nerve. Muscle in the engrafted region may be removed and frozen cross sections prepared. Immunolabeling can be performed on each muscle (e.g., TA muscle) sample using mouse monoclonal antibodies specific for human β-spectrin and human lamin A/C. Imaging can be performed.

3. EXAMPLE EMBODIMENTS

Example 1: Methods and Materials

Animals

Eight-week-old NOD-Rag1$^{null}$ IL2ry$^{null}$ (NOD-Rag) immunodeficient male mice (strain NOD.Cg-Rag1tm1Mom Il2rgtm1Wjl/SzJ; Jackson Laboratories, Bar Harbor, Me.) were used. These non-obese diabetic (NOD)-congenic mice harbor the Rag1$^{null}$ mutation on chromosome 2 and the IL2ry$^{null}$ mutation on the X-chromosome, which results in the absence of T, B and NK cells. This strain of mice is suitable for muscle xenografting as they tolerate high levels of irradiation-conditioning, avoid rejection of the transplanted human myoblasts, and hence allow efficient engraftment, differentiation and maturation of implanted myogenic cells (Silva-Barbosa et al., 2005). All protocols were approved by the Institutional Animal Care and Use Committee of the University of Maryland, Baltimore.

X-Ray Irradiation

The hindlimbs of young adult mice (8 weeks old) were subjected to a single, localized dose of X-radiation (25 Gy at 2.5 Gy/min) as described (Lovering et al., 2007). This dose has been previously shown to suppress >90% of satellite cell activation following CTX treatment (Roche at al., 2010). Other penetrating forms of ionizing irradiation or other treatments that effectively suppress muscle regeneration may be used. Briefly, mice were anesthetized by an intraperitoneal injection of a 2:1 mixture of 80 mg/kg ketamine (Butler Schein Animal Health, Dublin, Ohio) and 7 mg/kg xylazine (Akorn, Decatur, Ill.) and placed within a lead box. A person of ordinary skill in the art may use other anesthetics if determined to be appropriated and included but are not limited to isofluorane and 2-2-2-Tribromoethanol. The left hindlimb was exposed through a hole in the box for X-ray irradiation at a single dose of 25 Gy at 2.5 Gy/min. The hindlimb was secured with adhesive tape. The ionizing irradiation was delivered with a Pantak-Seifert 250 KpV X-Irradiator (bipolar series model HF 320, East Haven, Conn.). The radiation beam was focused onto the lower hindlimb while the rest of the body was protected by the lead shielding. Ion chamber dosimetry (PTW model 1006, Freiburg, Germany) was performed outside the collimator to ensure delivery of the exact dosage to the hindlimb, as well as inside the collimator (lead shielding), to monitor backscatter of radiation.

Cardiotoxin (CTX)

Mice were maintained under continuous anesthesia with 2%-2.5% isoflurane. A solution of 0.3 mg/ml cardiotoxin (CTS; *Naja mossambica* mossambica; Sigma, St. Louis, Mo.) was prepared in sterile phosphate saline buffer (1×PBS, 0.02% sodium azide) and filtered through a sterile 0.2 μm filter (PALL corporation; Port Washington, N.Y.). It is possible to use other toxins such as $BaCl_2$ and Notexin if preferred. CTX (0.3 mg/ml) was injected into three sites along the length of the TA muscle to allow wide distribution of the myotoxin, using a 300 μl 29-gauge tuberculin syringe (Terumo, Elktor, Md.) to give a final dose of 20 μg/10 gm body weight. CTX injection induces selective degeneration of endogenous myofibers without affecting the blood vessels or muscle innervation (Couteaux and Mira, 1985).

Human Myoblast Preparation and Transplantation

LHCN cells, hMPCs immortalized from satellite cells from a biopsy of the pectoralis major muscle of a 41-year-old male Caucasian heart-transplant donor, have been previously described (Zhou et al., 2007). This unique immortalized cell line was further transduced with retrovirus to express luciferase constitutively, to facilitate in vivo imaging of the grafted myoblasts.

Cells were grown in medium composed of four parts Dulbecco's modified Eagle's medium (Gibco, Life Technologies, Grand Island, N.Y.), to one part medium 199 (Gibco, Life Technologies, Grand Island, N.Y.), and supplemented with 15% HyClone USDA tested fetal bovine serum (Thermo Scientific, Rockford, Ill.), 0.02 M HEPES (Sigma-Aldrich, St. Louis, Mo.), 0.03 μg/ml zinc sulfate ($ZnSO_4$) (Fisher Scientific, Pittsburgh, Pa.), 1.4 μg/ml vitamin B12 (Sigma-Aldrich, St. Louis, Mo.), 0.055 μg/ml dexamethasone (Sigma-Aldrich, St. Louis, Mo.), 2.5 ng/ml human hepatocyte growth factor (HGF) (EMD Millipore, Billerica, Mass.), and 10 ng/ml basic fibroblast growth factor (bFGF) (BioPioneer, San Diego, Calif.) (Zhu et al., 2007). Cells were allowed to proliferate on dishes coated with 0.1% pigskin gelatin (Sigma-Aldrich, St. Louis, Mo.) until they reached 70%-80% confluency. Cells were maintained at 37° C. in 10% $CO_2$ atmosphere. Myogenic purity of cell cultures was determined following anti-desmin immunofluorescence staining (diluted 1/100; Thermo Scientific, Rockford, Ill.), as desmin protein is expressed in muscle cells and not fibroblasts. Each cell preparation used for transplantation reached 80%-85% myogenic purity.

Prior to injection, cells were released form the substrate by brief digestion with trypsin, diluted in an equal volume of growth media and centrifuged at $1 \times 10^3$ rpm for 3 min (IEC Centra CL2 centrifuge). Cells were suspended in 50 µl growth media.

Two concentrations of LHCN cells were injected: $5 \times 10^5$ (Group 1, n=18) or $2 \times 10^6$ (Group 2, n=21). Additionally some of the mice from Group 2 were subjected to intermittent neuromuscular electrical stimulation protocol (iNMES) to see if this increased the efficiency of engraftment (Group 3, n=16). Aliquots of cell suspensions containing human immortalized LHCN myoblast cells ($5 \times 10^5$ Group 1) or ($2 \times 10^6$ Group 2) were injected into the TA muscle compartment along the bone of NOD-Rag mice following X-irradiation and CTX muscle injury. The needle was withdrawn slowly from the knee towards the ankle, to promote broad distribution of the injected cells. A third experimental group was injected with 2×106 cells and subjected to neuromuscular electrical stimulation, as described below (Group 3).

Bioluminescence Imaging (BLI)

BLI was performed on a subset of animals using the Xenogen IVIS® 200 system (Caliper Life Sciences, Hopkinton, Mass.) to monitor the survival and development of the engrafted LHCN cells non-invasively. Mice were anesthetized with 2%-2.5% inhaled isoflurane. A solution of D-Luciferin (40 mg/kg) (Caliper Life Sciences, Hopkinton, Mass.) was prepared in sterile 1×PBS and sterilized by filtration through a 0.2 µm filter (PALL Corporation). Mice were injected intraperitoneally with the solution of D-luficerin at a dose of 150 mg/kg. Mice were returned to their cages for 5 min to allow luciferase biodistribution. Anesthetized mice were placed in a light-tight chamber and the light emitted from the LHCN-luciferase-expressing myoblasts through the TA grafted tissue was detected with a cooled charge coupled device camera. Imaging was performed 15 minutes after injection, when the luciferase activity reached its peak. A sequence of 12 scans with 5 min intervals were acquired (a total of 120 min), to determine the peak kinetic time. At regular intervals thereafter, usually on a weekly or biweekly basis, for 4 to 7 weeks, imaging was performed to assess the rate of loss of transplanted cells over time. Following the 4-week period after transplantation, animal images were acquired based on the determined peak kinetic value.

Regions of interest (ROI) encompassing the injected area of the TA tissue were selected and the luciferase-mediated light intensity was quantified using the LIVING IMAGE® 4.3.1 software (Caliper Life Sciences, Hopkinton, Mass.) and expressed as total counts of photons per second (photons/sec; total flux). The bioluminescence image (pseudo color image) was overlaid on a photographic image, with light intensity represented with a heat map (blue indicates the least intense and red most). The majority of the animals were scanned on day 0 (immediately after injection of LCHN myoblasts) and day 30 post transplantation and many were scanned at intermediate times.

Neuromuscular Electrical Stimulation (NMES)

NMES was performed to determine if it enhanced engraftment of LHCN cells. Previous studies have demonstrated improvement in myogenic potential of muscle precursor cells (Serena et al., 2008), muscle angiogenesis and muscle force (Ambrosio et al., 2012) in both in vitro and in vivo assays, respectively. Mice were anesthetized with 2%-2.5% isoflurane. The ankle dorsiflexors were stimulated by electrical pulsing through the intact skin over the common peroneal nerve over the head of the fibula. Monophasic square wave pulses of 0.1 ms duration were delivered to the stimulation electrode by an S48 Stimulator (Grass Instruments, Warwick, R.I.). A stimulation isolation unit (model PSIU6; Grass Instruments, Warwick, R.I.) was used to minimize artifact and to ensure that the peak current delivered was no greater than 15 mA. Each contraction was for 500 ms (150 Hz pulse frequency), followed by a 500 ms rest. A rest time of 2 min was followed between the sets of 10 contractions to minimize the effect of fatigue. NMES training was repeated four times (a total of 40 contractions), at a frequency of three times a week over a period of 4 weeks.

In Vivo Assessment of Contractile Function

The maximal torque generated by the ankle dorsiflexors in treated and control hindlimbs during tetanic stimulation of the peroneal nerve was measured in vivo (n=4 animals tested each time), as previously reported (Lovering et al., 2007; Roche et al., 2008; Roche et al., 2010). Briefly, mice were anesthetized with isoflurane (2%-2.5%) and the limb was stabilized onto a rig by a 27G needle placed transosseously through the head of the tibia. The foot was further placed onto a torque sensor pedal and stabilized with adhesive tape. The ankle dorsiflexors were engaged by stimulating the common peroneal nerve through the skin with an electrode using monophasic square pulses, 0.1 ms in duration, delivered by an S48 Stimulator (Grass Instruments, Warwick, R.I.). Pulse amplitude was adjusted to give maximal twitch tension, after which the optimal position of the ankle was determined by giving twitches (single stimuli) at different lengths of the dorsiflexors.

At resting length, the frequency of pulses in a 300 ms pulse-train were progressively increased until a maximal fused tetany was obtained; usually 100 HzA stimulation isolation unit (model PSIU6; Grass Instruments, Warwick, R.I.) was used between the stimulator and electrode to minimize artifact and to ensure that the peak current delivered is no greater than 15 mA. Three separate twitches and tetanic contractions were recorded and saved for further analysis. Signals from the torque sensor were amplified (inline amplifier model DV-05, Sensotec; Columbus, Ohio) and sent to a computer via a 12-bit analog to digital board (LabPC-1200, National Instruments; Austin, Tex.). Data were recorded using custom written software (Labview 4.1, National Instruments; Austin, Tex.). To assess functional recovery, the treated TA muscle was compared with control TA of the same animal. Contractile force was measured 4 weeks after transplantation.

Contractile force was measured similarly, with the following modifications. The skin on the limb to be assayed was peeled back to expose the lower half of the TA muscle. The TA tendon is lassoed with #4 braided silk thread. The remainder of the TA muscle is freed from surrounding tissue and tied via the thread to the foot plate, which is connected to a force transducer. The Extensor digitorum longus muscle is cut, and the isolated TA is then adjusted on the footplate to a resting tension of ~0.6 N/mm. Electrical stimulation is initiated from frequencies of 1-100 Hz and the tension is measured. Mineral oil is applied to the muscle surface, as needed, to prevent dehydration. TA muscle can be collected after this procedure for morphological and biochemical studies.

Histology and Immunofluorescence Labeling

Mice were euthanized by cervical dislocation. The TA muscle in the engrafted region was removed, weighed and embedded with O.C.T. (Tissue Tek; Torrance, Calif.), snap frozen in liquid nitrogen and stored at −80° C. Cryosections (10-15 μm thick) were cut and mounted on glass Superfrost microslides (VWR, Radnor, Pa.). Immunolabeling was performed on unfixed sections from every TA muscle sample, following standard laboratory methods.

Mouse monoclonal antibodies specific for human β-spectrin (1:100: Leica, Buffalo Grove, Ill.) and human lamin A/C (1:200: Leica, Buffalo Grove, Ill.) were used to label the sarcolemma and nuclear lamina, respectively of cells of human origin. To evaluate the internal organization of the newly formed human muscle fibers, sections were also stained with rabbit polyclonal anti-desmin (1:200: Thermo Scientific, Rockford, Ill.). To detect evidence of neuromuscular junction formation in the nascent myofibers, α-bungarotoxin conjugated with Alexa Fluor® 594 (Molecular Probes; Life Technologies, Grand Island, N.Y.) was used. (1:200: BIOSS). Presynaptic terminals were detected with antibodies to the SV2 antigen. Sections that were acetone-fixed and stained with a rabbit polyclonal antibody to collagens I/III (1:50; VWR, Radnor, Pa.) were used to detect matrix collagens.

To reduce non-specific staining due to the reaction of primary mouse monoclonal antibodies with the endogenous mouse tissue's immunoglobulins, sections were treated with reagents the Mouse-on-Mouse (M.O.M) kit from Vector Laboratories (Burlington, Calif.). Briefly, sections were incubated for 1 hour with M.O.M. blocking reagent and further with M.O.M. diluent protein concentrate solution at room temperature (RT) for 10 min. After three washes in 1×PBS-BSA (1 mg/ml) for 5 min each, sections were incubated overnight at 4° C. with primary antibodies diluted in the solution of protein concentrate. After three washes in 1×PBS-BSA (1 mg/ml) for 5 min each, primary mouse and rabbit antibodies were visualized with Alexa fluor 488 donkey anti-mouse IgG (H+L) and Alexa fluor 568 donkey anti-rabbit IgG (H+L) 568, respectively, (1:200: Molecular Probes; Life Technologies, Grand Island, N.Y.) following 1-2 hours incubation at RT. Sections were washed three times in 1×PBS supplemented with 1 mg/ml BSA for 5 min each, and mounted in Vectashield mounting medium with DAPI (4',6-Diamidino-2-Phenylindole, Dihydrochloride) (Vector Laboratories, Burlingame, Calif.).

Sections were viewed using a Zeiss LSM5 DUO confocal microscope, with 40× or 63× objectives (Carl Zeiss, Germany). Images were digitalized using LSM Image browser analysis system. Myofibers of human origin, identified by peripheral labeling with antibodies against human β-spectrin were counted. The size of human myofibers was determined by measuring minimum Feret's diameter (Briguet et al., 2004). Based on their measured sizes, myofibers were divided into three groups (1-9 μm, 10-19 μm and ≥20 um). For each TA sample, the percent of myofibers within each group was calculated and compared between the groups. Distances from the largest human myofibers to each of its neighboring myofibers were measured. Additional morphometric assessment of the engrafted human myofibers was performed using LSM Image browser analysis system. These measurements included the number of nuclei positive for human lamin A/C (Riederer et al., 2012; Skuk et al., 2010; Negroni et al., 2009; Silva-Barbosa et al., 2008), the number of murine myonuclei in myofibers of human origin, identified as myonuclei labeled by DAPI but not by antibodies to human lamin A/C, and the number of centrally nucleated myofibers.

Statistical Analysis

To compare the total count of donor-derived myofibers between the experimental groups, data were analyzed using one-way analysis of variance (ANOVA). The sizes of the engrafted human myofibers across the experimental groups were analyzed with the chi-square test and the intermyofiber distance between the largest engrafted myofibers and their closest neighboring myofibers was evaluated with Fisher exact tests. Data are presented as the mean±SD or ±SEM. A P value of <0.05 was considered significant.

Example 2: In Vivo Bioluminescence Imaging Reveals Acute Donor Cell Loss within the First Week Following LHCN Transplantation BLI was performed to evaluate qualitatively the engraftment efficiency and quantify the survival of engrafted human myogenic precursor cells (hMPCs) into the TA compartment of the mouse hindlimb. Treated TA muscle prior to LHCN injection is significantly reduced in size (not shown). X-irradiation and cardiotoxin treatment therefore effectively eliminated the mouse TA muscle and prevented it from regenerating. Serial images of the mice were performed on Day 0 after the injection of the LHCNs, and then typically at 1, 2, and 4 weeks post-transplantation. Some mice were also examined at 7 weeks post-engraftment.

Quantitative analysis of the bioluminescence signal was detected as a function of time after LHCN transplantation. Luminometry of engrafted mice is illustrated in FIG. 1A-D. FIG. 1A-1D illustrate bioluminescent images of mice, 100, at time periods including day 0, 102, and day 7, 104, day 28, 106 and day 49, 108, after injection of LHCN cells. Signals detected in the TA compartment are indicated in pseudo-color, 110.

Injection of $5\times10^5$ or $2\times10^6$ LHCN human myoblasts into the X-irradiated and cardiotoxin (CTX) pre-treated TA muscles (Groups 1 and 2, respectively) resulted in a robust, though variable, bioluminescence signal at day 0 (not shown). High levels of bioluminescence were also detected for Group 3 (injection of $2\times10^6$ LHCN myoblasts followed by NMES training).

Figure 2:
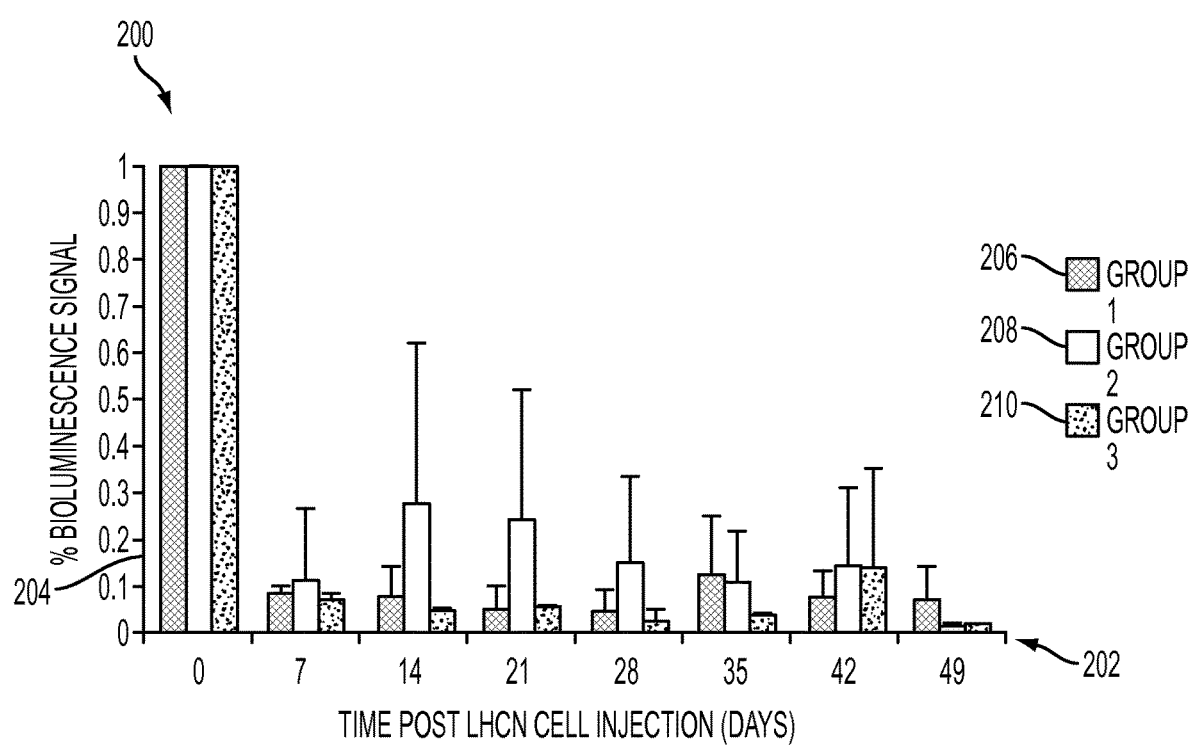
FIG. 2 is a graph illustrating quantitative analysis of bioluminescence as a function of time following transplantation, according to an embodiment.

Luminometric measurements of LHCN survival are shown in FIG. 2 In FIG. 2, the graph 200, having an x-axis, 202, and a y-axis, 204, shows the quantitative analysis of bioluminescence as a function of time following transplantation, reported as a percentage of the signal on day 0 for Group 1 mice, 206, Group 2 mice, 208, and Group 3 mice, 210. Within the first week post-transplantation, ~10% of the original signal originating in the injected LHCN remained for all three groups studied. This indicates that the majority of the injected myoblasts in all 3 groups failed to survive. At 7 weeks post LHCN transplantation only ~5% of the bioluminescence signal seen after the initial injection of LHCN cells was detected in the TA compartments. It should be noted that a combination of increased number of LHCN cells ($2\times10^6$) and neuromuscular electrical stimulation (NMES) training at day 7 post injection (Group 3), resulted in no significant improvement of the bioluminescence signal.

Taken together, these findings indicate long-term survival of some the engrafted LHCN cells, however, with a small percent of engrafted cells (≤7%) retained in the mouse TA compartments at 7-8 weeks post transplantation.

Example 3: Assessment of Functional Recovery of the LHCN-Transplanted TA Muscles Torque and force measurements were performed at four weeks after human myoblast transplantation to investigate the ability of the grafts formed by the injected LHCN cells to contract LHCN-transplanted TA muscles following injection of 2×10⁶ myoblasts with (Group 3) or without NMES treatment (Group 2). The values for the two groups were not significantly different from each other (not shown). They were, however, significantly weaker than TA compartments in mice that were not X-irradiated, and therefore recovered much of their contractile activity following treatment with CTX (not shown).

Without being bound by theory, it is suggested that mouse TA xenografts, independently of the original amount of LHCN cells injected, generated significant but variable levels of contractile force which made it difficult to measure their contractile function in a statistically reliable manner. As a result of this variability, it is not possible to determine if NMES provided significant beneficial effects on the ability of the transplanted LHCN cells to generate contractile force.

Example 4: Immunohistological Analysis Revealed LHCN Myoblast Engraftment and Maturation into Myofibers Engrafted TA muscle tissues were collected at 4 weeks after injecting the LHCN cells and characterized. The mass of the engrafted muscle was compared with that of the control mouse TA muscle. Morphological assessment of the LHCN-transplanted TAs preconditioned with X-irradiation and CTX varied in size from 4 to 14 mg in mass (9.9+/−6.1 mg for Group 1; 9.1+/−2.7 mg for Group 2; 12.5+/−11.6 for Group 3; mean+/−SD). These differences were not statistically significant. The variability is consistent with the variability in our measurements of contractile torque and force, however. By contrast, murine TA muscles have a mass of 31-51 mg (43.2+/−2.8 mg, mean+/−SD).

Characterization of Myofibers of Human Origin

Figure 3:
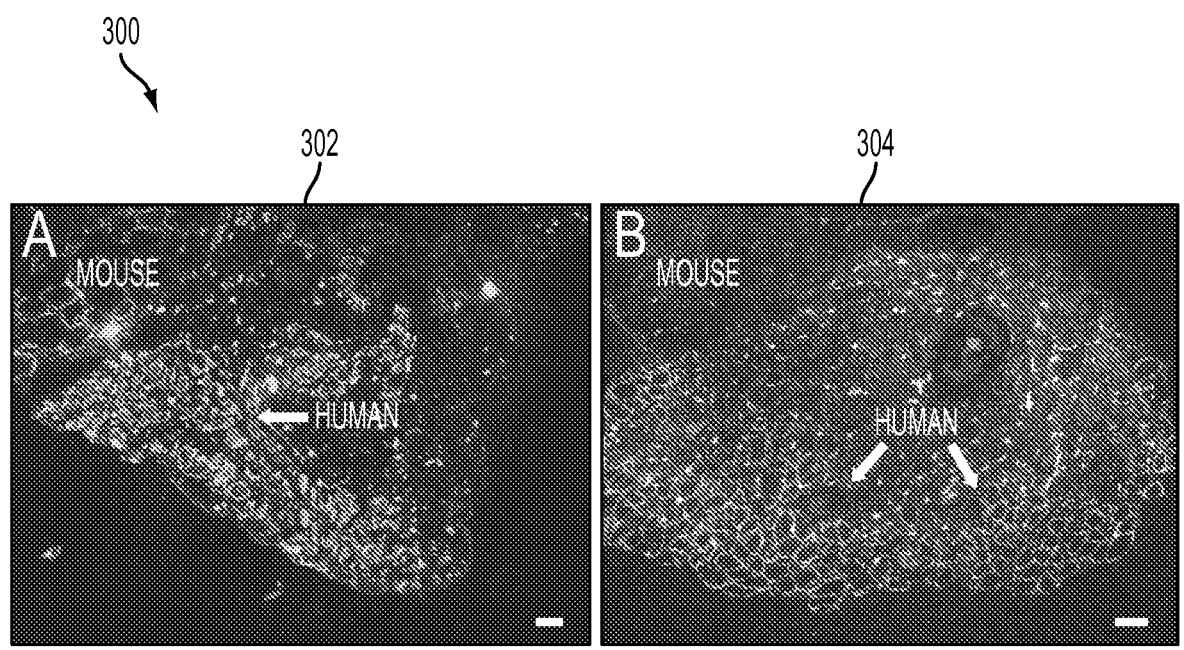
FIG. 3A-3B are fluorescent images illustrating human muscle fibers in engrafted limbs collected at 4 weeks after injection of $2.5 \times 10^5$ LHCN cells, according to an embodiment.

Frozen cross sections of the human muscle grafts from Groups 1, 2, and 3 were prepared. Monoclonal antibodies specific for human β-spectrin were used to label the sarcolemma of the myofibers in the engrafted region to determine if they developed at least in part by the fusion of LHCN cells. FIG. 3A-3B show photographs, 300, of myofibers that are at least partially of human origin in mice that were either treated, 302, (Group 3, FIG. 3A), or not treated, 304 (Group 2, FIG. 3B) with NMES. At 4 weeks post-transplantation, significant numbers of myofibers of human origin were found in Groups 2 and 3, injected with 2×10⁶ LHCN cells, but not in Group 1, injected with 5×10⁵ LHCN cells (not shown; but see FIG. 4). The results suggest that NMES treatment for 4 weeks following injection of 2×10⁶ LHCN cells (Group 3) results in grafts that contain more human muscle fibers that were larger in size and more closely packed together than grafts that formed in mice that were not subjected to NMES (Group 2). These qualitative conclusions were quantitated below.

Figure 4:
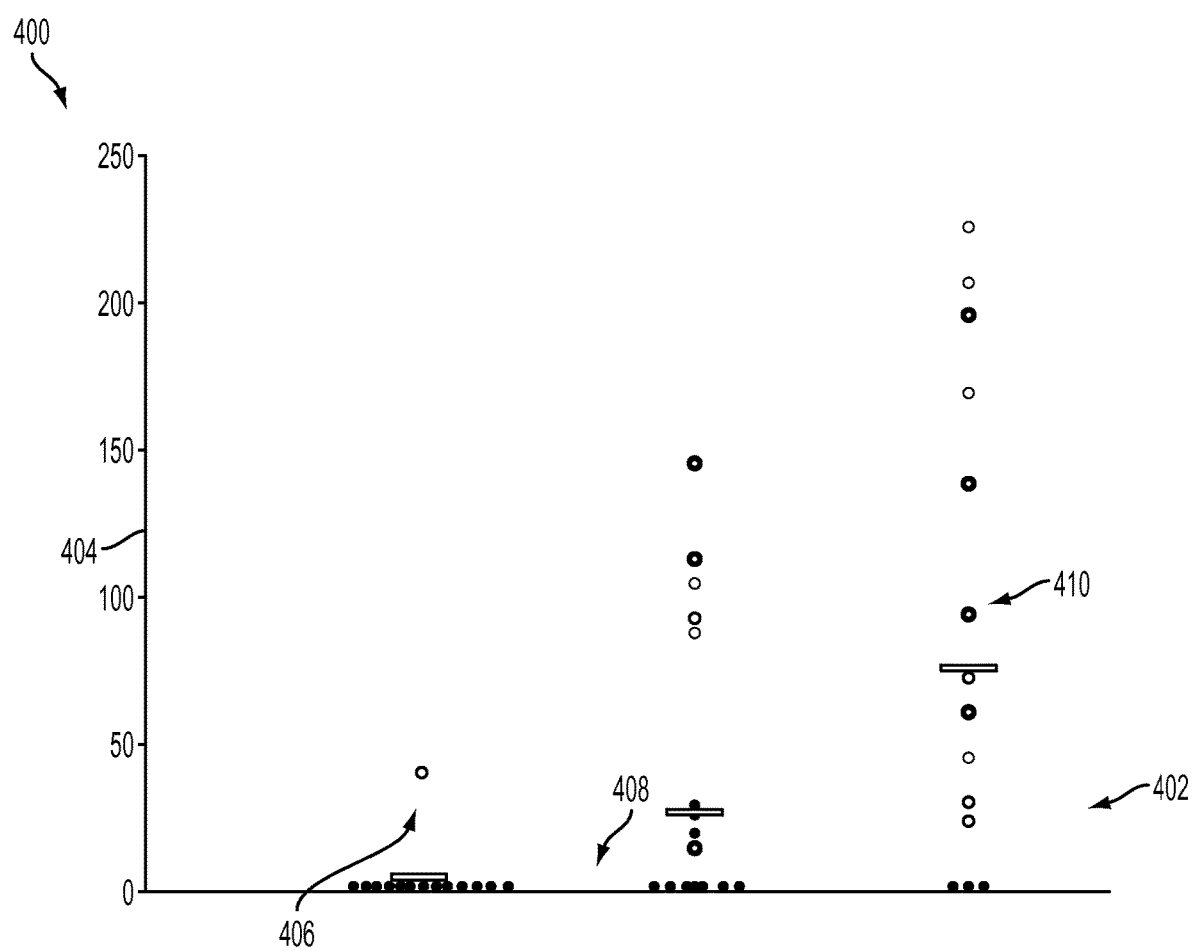
FIG. 4 is a graph illustrating the number of muscle fibers of human origin per graft after injection of $5 \times 10^5$ and $2.5 \times 10^6$ LHCN cells, according to an embodiment.

FIG. 4 is a graph, 400, with an x-axis, 402, and a y-axis, 404, that illustrates the number of fibers that labeled with antibodies to human β-spectrin that we counted in each graft. The results show that injection of 5×10⁵ LHCN cells, 406, yielded only one mouse in which a significant number of myofibers of human origin were detected, with the remaining 13 mice showing no such myofibers. Injection of 2×10⁶ LHCN cells yielded many more fibers of human origin, however. In Group 2, 9 of 15 mice had significant numbers of myofibers that labeled with antibodies to human β-spectrin, 408, whereas in Group 3, 11 of 14 mice had fibers of human origin, 410. Comparisons of all 3 groups showed that the differences in the numbers of mice containing grafts with fibers of human origin, and the numbers of fibers in these grafts were both statistically significant. In particular, Group 3 had a mean±SD number of fibers of 82.2±79.2, compared to Group 2, with 30.9±46.3 ($p<0.05$). The largest number of human myofibers in LHCN-generated grafts is 226, or approximately 10% of the number of myofibers in a normal mouse TA muscle (Sharp et al., 2011). These results confirm that injection of 2×10⁶ LHCN cells, but not 5×10⁵ LHCN cells, reliably yields grafts containing myofibers of human origin, and that NMES further enhances the formation of such grafts and increases the number of human myofibers in them.

Figure 5:
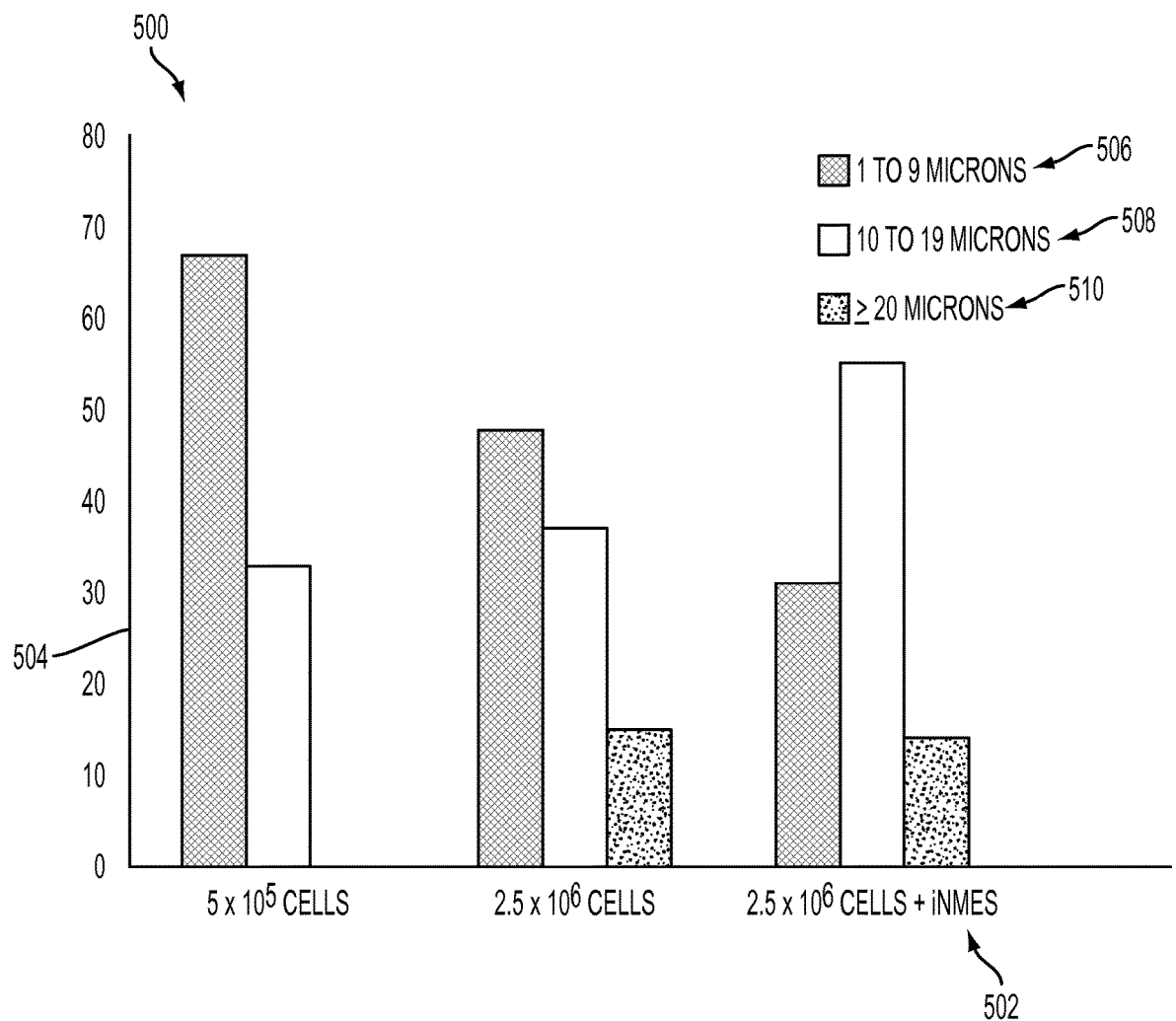
FIG. 5 is a graph illustrating the sizes of human myofibers in grafts after injection of $5 \times 10^5$ LHCN cells, $2.5 \times 10^6$ LHCN cells, and $2.5 \times 10^6$ LHCN cells plus NEMS, according to an embodiment.

FIG. 5 is a graph, 500, with an x-axis, 502, and a y-axis, 504, that illustrates the differences the sizes of the myofibers of human origin in the grafts. In the sole graft containing human myofibers in Group 1, injected with 5×10⁵ LHCN cells, almost 70% of the myofibers were 9 μm or less in diameter, 506, and the largest myofibers did not exceed 19 μm in diameter, 508. By contrast, more than 10% of the myofibers of human origin in Groups 2 and 3 were 20 μm or more in diameter, 510, and approximately half (Group 2) or 70% (Group 3) of the fibers were 10 μm or more in diameter, 508, 510. Although the mean values measured for minimal Feret's diameter in Group 2, 12.4±7.06 μm, and in Group 3, 13.05±6.3 μm, were very similar, there was a significant increase in the number of larger myofibers in size in Group 3 over Group 2 ($p<0.00001$). These results confirm that injection of 2×10⁶ LHCN cells, but not 5×10⁵ LHCN cells, reliably yields grafts containing large myofibers of human origin, and that NMES increases the number of large human myofibers in the grafts.

Figure 6:
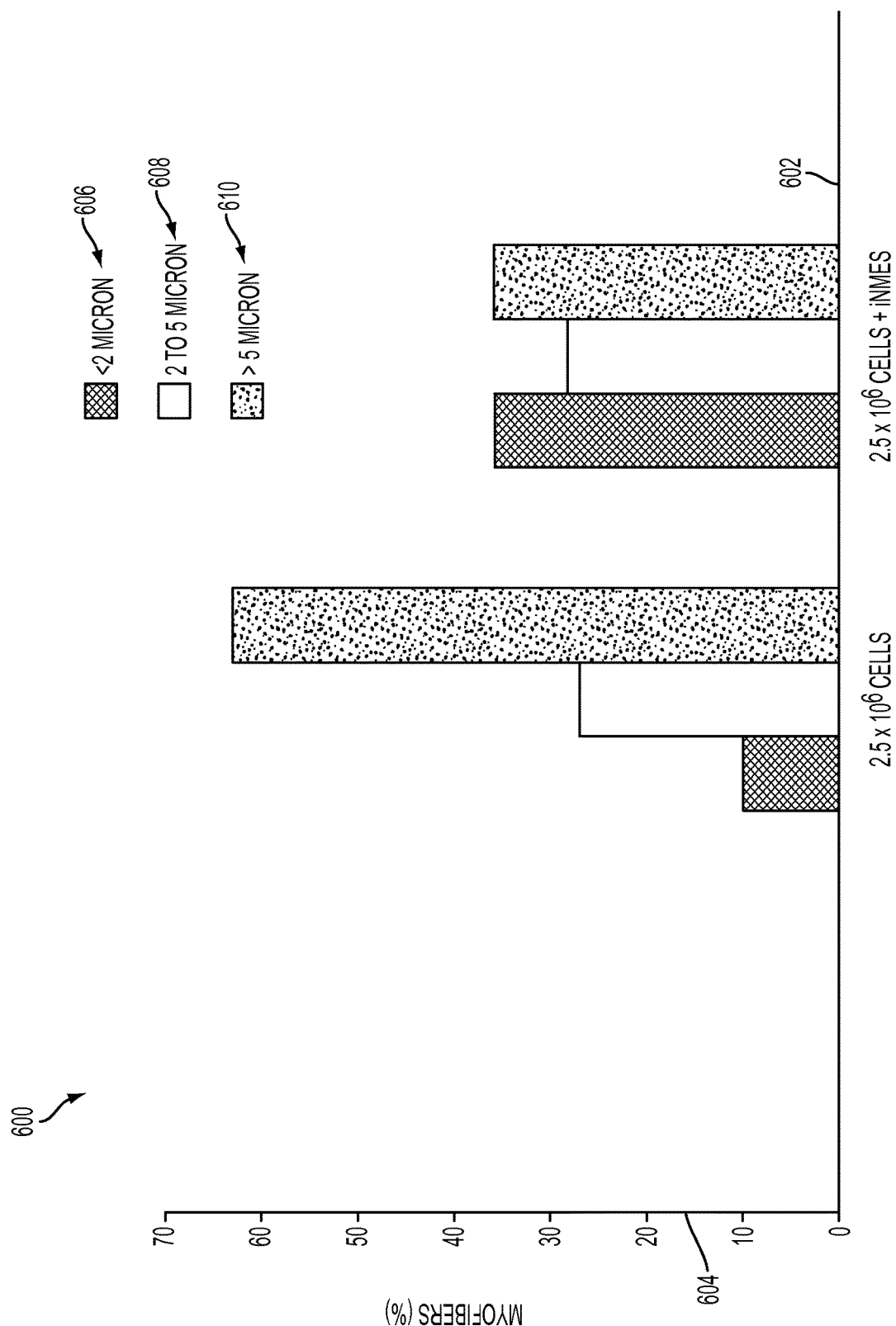
FIG. 6 is a graph illustrating the distances between the largest fibers of human origin in each graft and each of their nearest neighbors of human origin after injection of $2.5 \times 10^6$ cells and $2.5 \times 10^6$ cells plus NMES, according to an embodiment.

FIG. 6, is a graph, 600, having an x-axis, 602, and a y-axis, 604, that shows measurements of the distances between the largest human myofibers in the grafts of Group2 and Group 3 and each of their nearest neighbors. Distances were measured as <2 μm, 606, 2 to 5 μm, 608, and >5 μm, 610. In Group 2, the highest percentage of myofibers (60%) was greater than 5 μm away from the nearest myofiber. Conversely, in Group 3 only about 35% of myofibers were >5 μm. Similarly, in Group 2, only ~10% of the myofibers of human origin were <2 μm from their nearest neighboring fibers, whereas in Group 3 this value was ~35%. Overall, the interfiber distances in Group 3, 3.8±3.1 μm, were significantly less than those in Group 2, 7.0±5.6 μm ($p<0.0001$), Although the intermyofiber distances in Group 3 were greater than in healthy skeletal muscle (typically <1 μm, these results confirm that the grafts formed by 2×10⁶ LHCN cells followed by NMES (Group 3) were more tightly organized than those formed by the injection of the same number of cells but without NMES treatment (Group 2).

Presence of Collagen in Grafts

Figure 7:
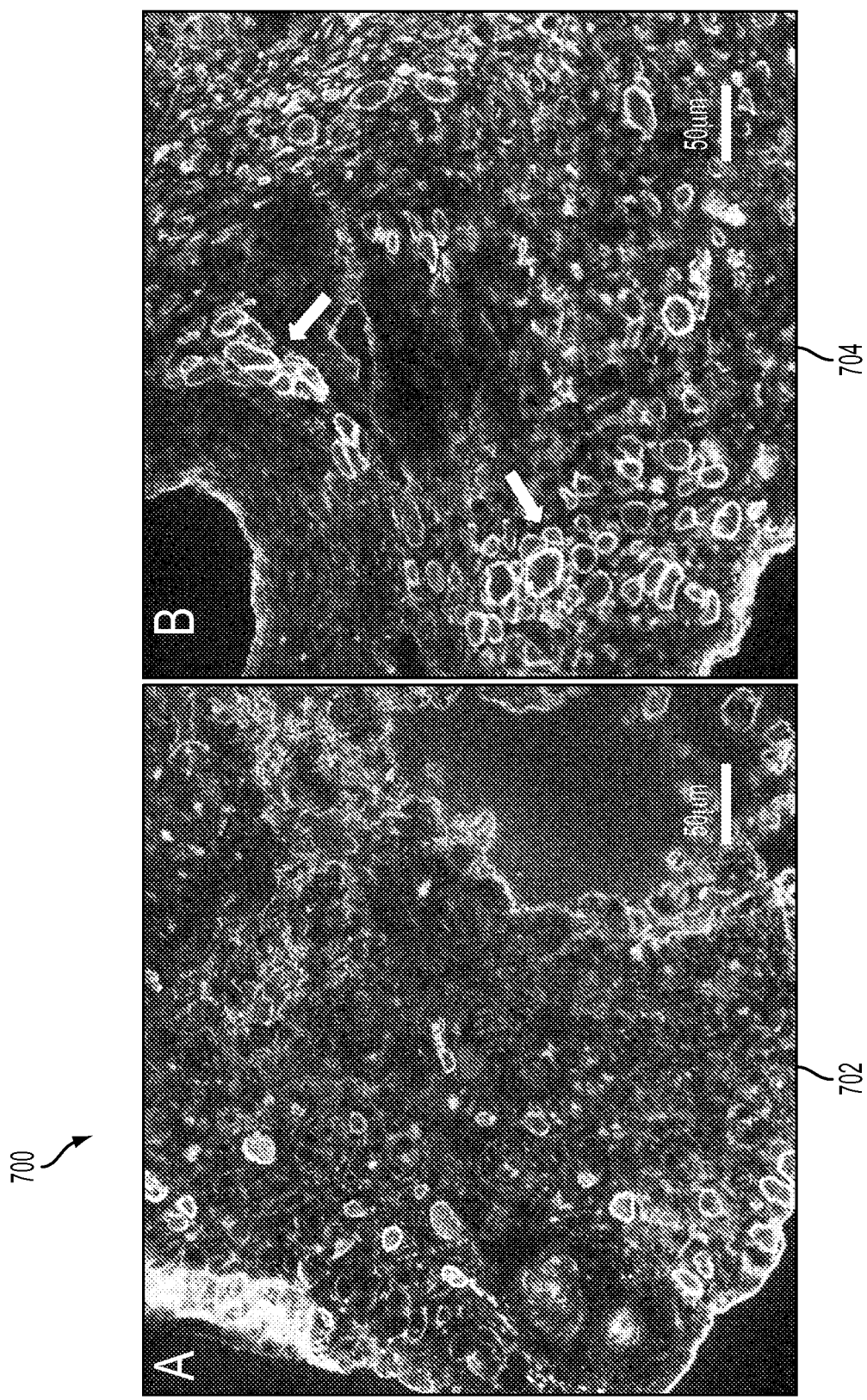
FIG. 7A-7B are fluorescent images illustrating the presence of collagen and fibrosis in human muscle grafts after injection of $2 \times 10^6$ LHCN cells and $2 \times 10^6$ LHCN cells plus NMES, according to an embodiment.

The connective tissue formed in the engrafted regions was also examined. Due to variability in the overall morphology of the LHCN-transplanted TA muscles, quantification of the extent of collagenous tissue in the engrafted regions was not possible. Therefore, only qualitative assessment of fibrosis was made across experimental groups 2 and 3. FIG. 7A-7B illustrate, 700, immunofluorescence staining with antibodies to collagen I and III and revealed less collagenous materials surrounding the engrafted human myofibers in Group 3 compared with Group 2 (FIG. 7A-7B). The amount of collagen present and labeled by the antibodies seems to increase as the distances between neighboring fibers increase, consistent with the presence of fibrotic tissue in those gaps. Collagen staining revealed more extensive fibrosis in the human muscle grafts that were not (FIG. 7A) subjected to NMES, 702, than in those that were (FIG. 7B) subjected to NMES, 704. The regions between myofibers in grafts subjected to iNMES contained far less labeling collagen then untreated grafts, consistent with the closer packing of myofibers promoted by NMES. Without being bound by theory, the formation of larger, more tightly packed fibers in Group 3 is associated with a reduction in fibrosis.

Differentiation of Fibers of Human Origin in the Graft

Figure 8:
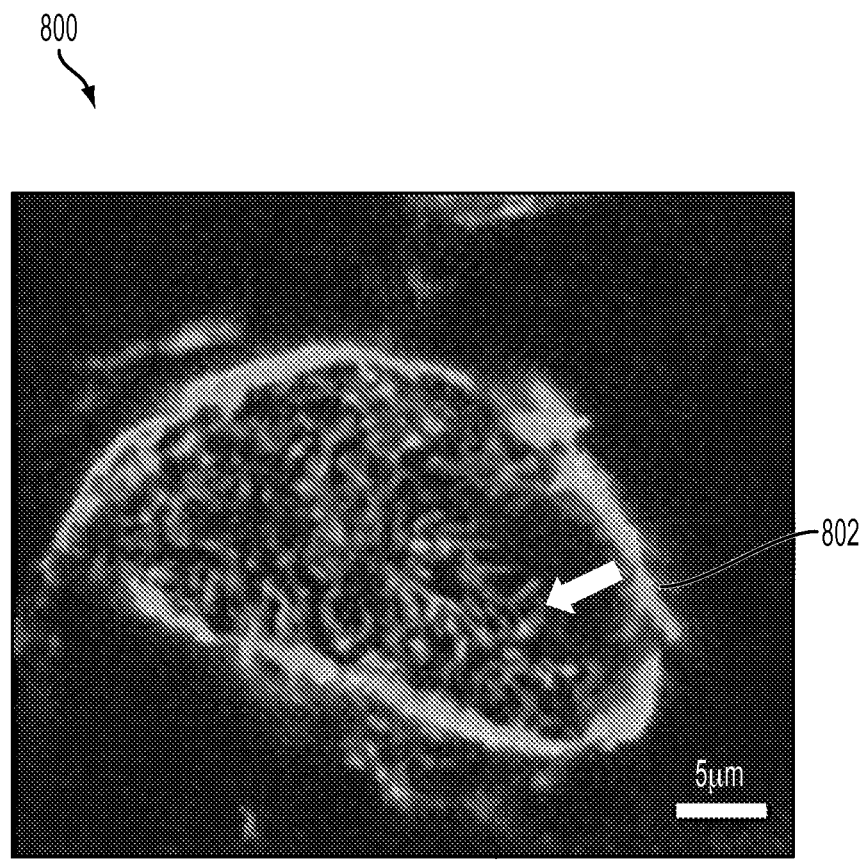
FIG. 8 is a fluorescent images illustrating organization of desmin in fibers of human origin after injection of $2 \times 10^6$ LHCN cells and $2 \times 10^6$ LHCN cells plus NMES, according to an embodiment.

In LHCN-transplanted TAs from Group 3, FIG. 8 is a photograph that illustrates immunofluorescence staining, 800, of many engrafted human myofibers and shows evidence of large, clear cytoplasmic networks of desmin in the myoplasm, 802, suggesting an organization of the contractile apparatus into myofibrils that are surrounded by a network of intermediate filaments composed at least in part of desmin. This is a late stage in myogenesis, indicating considerable maturity of the tissue formed by the engrafted cells (Capetanaki et al., 2007). Similar reticular networks of desmin were observed in cross-sections of the largest myofibers in Group 2 (not shown). These results indicate that the contractile apparatus in the large fibers of human origin in the grafts is differentiated, as it is in mature mammalian muscle.

Figure 9:
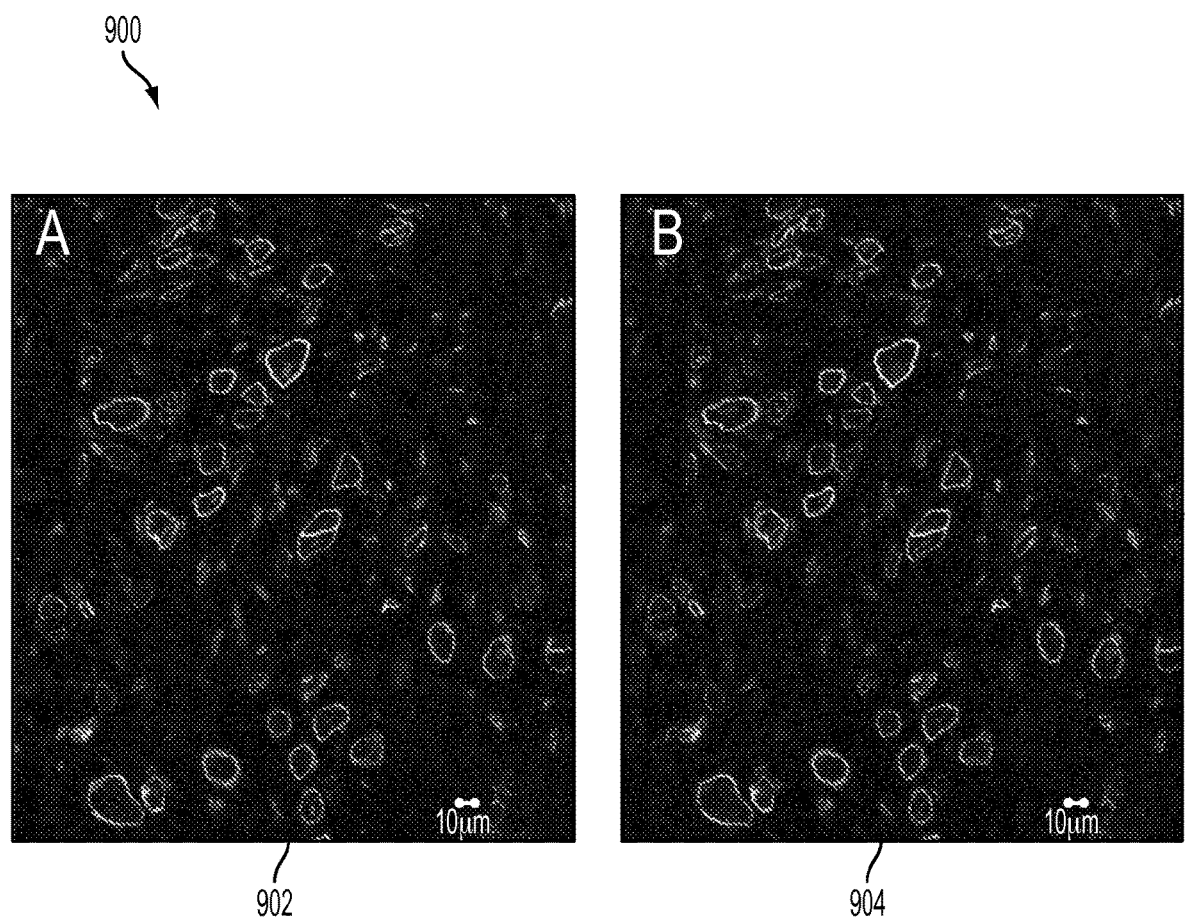
FIG. 9A-9B are fluorescent images illustrating quantitation of central nuclei of human and mouse origin in fibers of human origin, according to an embodiment.

It was confirmed that many of the fibers of human origin in the graft were terminally differentiated by labeling with DAPI, a nuclear stain. FIG. 9A-9B are photographs, 900, illustrating immunofluorescence images of central nuclei in fibers of human origin. Samples were labeled with antibodies to human lamin A/C, 902, as well as with antibodies to human β-spectrin, 904. In developing or regenerating muscle tissue, nuclei were frequently found in the middle of the cell, whereas in mature, fully differentiated muscle tissue, nearly all of the myonuclei were located peripherally, immediately adjacent to the sarcolemma. Examination of the grafts formed by LHCN cells showed that 82% (121 of 149) and 79% (146 of 185) of the myonuclei in the grafts were located peripherally in Groups 2 and 3, respectively, and that the remaining ~20% of the myonuclei in both groups were centrally located. Thus, by this criterion ~20% of the fibers are in the process of developing or regenerating, while ~80% were fully differentiated.

These results suggested that the engrafted LHCN cells were capable of terminally differentiating into mature muscle during the 4-week post transplantation period, and that, although this ability of the grafts to form myofibers that are >20 µm in diameter is promoted by NMES, NMES is not strictly required for the differentiation of myofibers in the graft.

Figure 10:
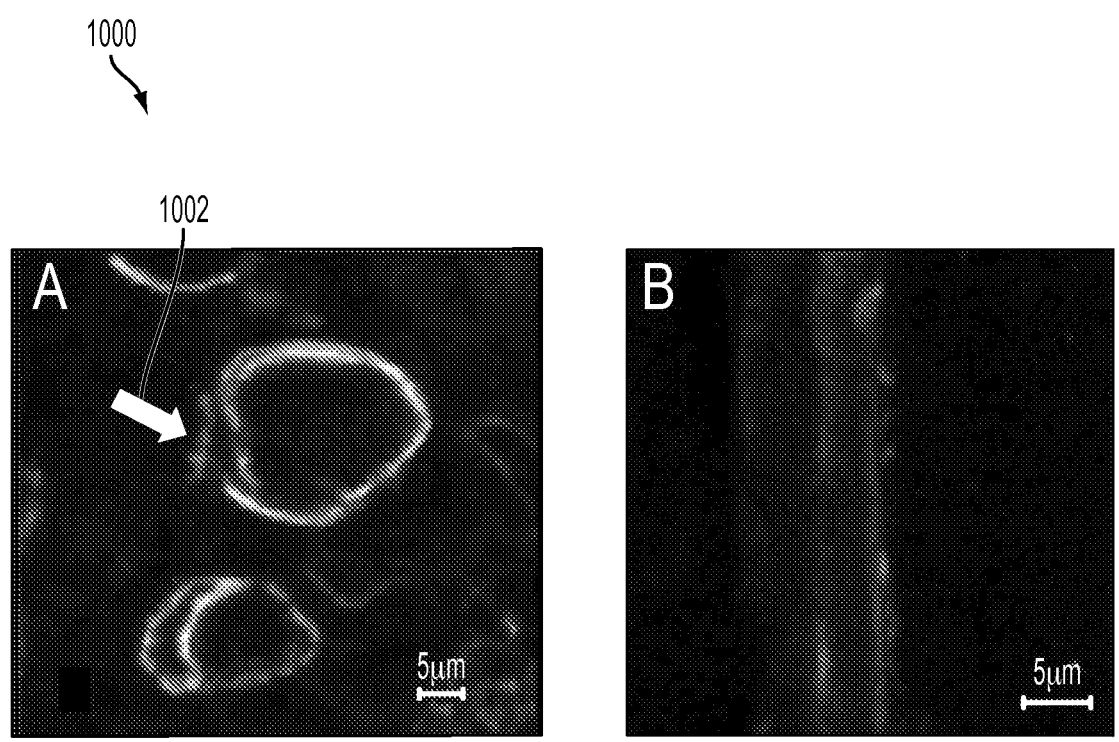
FIG. 10A-10B are fluorescent images illustrating neuromuscular junctions in grafts treated with iNMES, according to an embodiment.

The presence of differentiated myofibers of the size found in the xenografts suggested that the fibers formed by LHCN cells were innervated. In the absence of innervation, these fibers would atrophy significantly, and would consequently be greatly reduced in size. To test for innervation, the grafts of Group 3 were labeled with a fluorescent derivative of α-bungarotoxin, to detect the large clusters of acetylcholine receptors in the postsynaptic membrane of the neuromuscular junction. Structures typical of postsynaptic membrane that labeled by α-bungarotoxin on muscle fibers of human origin were found, indicating that innervation had occurred within 4 weeks after transplantation of LHCN cells. FIG. 10A-10B are photographs, 1000, that illustrate immunofluorescence staining of labeling of the post-synaptic membrane of the neuromuscular junction, 1002, in grafts treated with iNMES or with antibodies to SV2 antigen to label presynaptic structures, 1004. Immunolabeled sections were also examined with antibodies to SV2, a protein found in presynaptic vesicles at motor nerve terminals. SV2 was found in structures typical of nerve terminals lying along muscle fibers of human origin, consistent with the innervation of these fibers in the xenografts.

It was considered a possibility that, despite the fact the hindlimbs of mice were irradiated to prevent muscle regeneration following CTX intoxication, the myofibers formed by LHCN cells were hybrids formed by the fusion of the LHCN cells not only with each other but also with mouse myoblasts. In the absence of a mouse-specific lamin A/C antibody, mouse myonuclei were identified as those DAPI-stained myonuclei within myofibers that stained positively for human β-spectrin. To avoid any ambiguity in distinguishing peripheral myonuclei from nuclei of nearby cells, such as those in fibroblasts, capillaries and lymphocytes, analysis was limited to central nuclei, such as those shown in FIG. 9. The numbers of centrally located nuclei of mouse origin was extremely low in the human myofibers formed by LHCN cells in both in Group 2 (1/149, 1.3%), and Group 3 (5/185, 2.7%). These results suggest that there was minimal murine contamination of the human myofibers formed by LHCN cell grafts.

Consistent with these results, qualitative assessment of the human muscle grafts across the three experimental groups revealed that the vast majority of the mouse myofibers were ablated following X-irradiation and CTX treatment. Those remaining were typically at the edge of the xenograft containing human muscle tissue, suggesting that the latter was free of mouse muscle tissue. Therefore, the combination of X-irradiation and CTX treatments of the mouse TA muscle not only eliminates all or nearly all of the tissue of murine origin, but also inhibits the formation of hybrid human-mouse myofibers formed by transplantation of the LHCN myoblasts.

Repopulation of Engrafted LHCN Cells

Finally, data further suggested that the engrafted LHCN cells may have begun to repopulate the satellite cell niche in the graft. Donor-derived mononucleate cells co-expressed Pax7 and human lamin A/C associated with DAPI-positive nuclei at the periphery of myofibers of human origin (data not shown). This is the expected location of satellite cells. The ability of human muscle precursor cells to repopulate the satellite cell niche following introduction into mouse TAs was previously reported (Skuk et al., 2010).

4. OTHER EMBODIMENTS

Methods for Treatment of Muscle Disorders by Enhancing Myoblast Cell Engraftment to Generate Mature Muscle Fibers In certain embodiments, a subject having a muscle disorder is identified. The subject may be a mammal such as a mouse or human. If the mammal is non-human such as a mouse, the non-human mammal must be immunocompromised so that it does not reject injection of hMPCs. hMSCs are used to regenerate, repair, or newly generate muscle that has been damaged through disease or degeneration. In certain embodiments, hMPCs differentiate into muscle cells and integrate with the healthy tissue of the recipient to replace the function of the dead or damaged cells, thereby repairing and/or regenerating the muscle tissue as a whole. Reduced muscle function can be caused by a number of muscle diseases including, but not limited to those listed in Table 1.

hMPCs are injected into the portion of the limb. In certain embodiments, hMPCs of different origins, distinct from LHCN cells, may be injected. hMPCs may be injected at different times after irradiation and intoxication, at different doses and frequencies, and over a different time course, as determined by one of skill in the art. In some aspects, injection can be provided by several routes of administration, including but not limited to, intramuscle injection, if the hMPCs are in a liquid suspension preparation or where they are in a biocompatible medium which is injectable in liquid form. A conventional intramuscle syrine can serve as a delivery device and can buse used so long as the needle lumen or bore is of sufficient diameter so as to not damage the hMPCs. The injectable hMPCs can also be administered intravenously either by continuous drip or as a bolus. The nerve of the limb (e.g, pereoneal nerve) is subjected to therapeutic electrical stimulation such as NMES or other means such as exercise (e.g., running wheel in a cage or on a treadmill) configured to enhance engraftment of the myogenic precursor cells.

As a representative example of a dose range in a nonhuman mammal such as a mouse is a volume of at least about $2 \times 10^6$ hMPCs in 50 µl into the former TA region. For humans, the dosage would be configured by one of ordinary skill in the art depending on necessity due to the health of the subject, extent of muscle disease, muscle injury, and degree of loss of function.

In certain embodiments, the subjects may be rendered incapable of rejecting the engrafted hMPCs by x-irradiation or by genetic means or by means other than genetic means. Such means may include, but are not limited to, other forms of radiation or treatment with a drug that suppresses the immune system. Different doses and time courses for x-irradiation and these other means used to suppress the myogenic potential of the muscle in the subject and are known in the art. Engrafted limbs may be treated in certain embodiments with drugs, hormones, or other biologically active compounds or materials to promote engraftment. Such reagents ma include, but not be limited to, losartan, IFG1, antibodies to TGF-β proteins, and the region of the ActRIIB receptor that binds proteins of the TGF-β superfamily.

TABLE 1

Muscle Diseases amyotrophic lateral sclerosis (ALS)
Andersen Tawil Syndrome
Becker Muscular Dystrophy (BMD)
Becker Myotonia Congenita
Bethlem Myopathy
Bulbospinal Muscular Atrophy (Spinal Bulbar Muscular Atrophy)
Carnitine Deficiency
Central Core Disease (CCD)
Centronuclear Myopathy
Charcot Marie Tooth Disease (CMT)
Congenital Muscular Dystrophy (CMD)
Congenital Myotonic Dystrophy
Dejerine-Sottas Disease (DSD)
Dermatomyositis (DM)
Distal Muscular Dystrophy (DD)
Duchenne Muscular Dystrophy (DMD)
Dystrophia Myotonica (Myotonic Muscular Dystrophy)
Emery-Dreifuss Muscular Dystrophy (EDMD)
Eulenberg Disease (Paramyotonia Congenita)
Facioscapulohumeral Muscular Dystrophy (FSH or FSHD)
Finnish (Tibial) Distal Myopathy
Fukuyama Congenital Muscular Dystrophy
Glycogenosis Type 4 (fetal only, in humans; identified in cats, too)
Hauptmann-Thanheuser MD (Emery-Dreifuss Muscular Dystrophy)
Hereditary Inclusion-Body Myositis
Hereditary Motor and Sensory Neuropathy (Charcot-Marie-Tooth Disease)
Hyperthyroid Myopathy
Hypothyroid Myopathy
Inclusion-Body Myositis (IBM)
Inherited Myopathies
Integrin-Deficient Congenital Muscular Dystrophy
Kennedy Disease (Spinal-Bulbar Muscular Atrophy)
Kugelberg-Welander Disease (Spinal Muscular Atrophy)

TABLE 1-continued

Muscle Diseases

Limb-Girdle Muscular Dystrophies (LGMDs)
Lou Gehrig's Disease (Amyotrophic Lateral Sclerosis)
Merosin-Deficient Congenital Muscular Dystrophy
Metabolic Diseases of Muscle
Mitochondrial Myopathy
Miyoshi Distal Myopathy
Motor Neurone Disease
Muscle-Eye-Brain Disease
Myasthenia Gravis (MG)
Myofibrillar Myopathy
Myotonia Congenita (MC)
Myotonic Muscular Dystrophy (MMD)
Myotubular Myopathy (MTM or MM)
Nemaline Myopathy
Nonaka Distal Myopathy
Oculopharyngeal Muscular Dystrophy (OPMD)
Paramyotonia Congenita
Periodic Paralysis
Peroneal Muscular Atrophy (Charcot-Marie-Tooth Disease)
Polymyositis (PM)
Pompe Disease (Acid Maltase Deficiency)
Progressive External Ophthalmoplegia (PEO)
Rod Body Disease (Nemaline Myopathy)
Spinal Muscular Atrophy (SMA)
Spinal-Bulbar Muscular Atrophy (SBMA)
Steinert Disease (Myotonic Muscular Dystrophy)
Thomsen Disease (Myotonia Congenita)
Ullrich Congenital Muscular Dystrophy
Walker-Warburg Syndrome (Congenital Muscular Dystrophy)
Welander Distal Myopathy
Werdnig-Hoffmann Disease (Spinal Muscular Atrophy)

In some aspects, the present invention generally relates to methods of generating mature human muscle fibers in vivo i.e., in mice, free from murine myonuclei, and similar in size to mouse muscle fibers. In one embodiment, the invention provides a method of generating mature human muscle fibers in a non-human animal such as a mouse comprising: a) removing the non-human or mouse muscle e.g., TA muscle and preventing it from regenerating, b) injecting human myogenic cells into a portion of a limb of the non-human animal or into the volume previously occupied by the muscle, and c) subjecting the peroneal nerve of the injected limb to electrical stimulation in vivo. Electrical stimulation has long been known to promote muscle differentiation in vitro (e.g., DeDeyne, 2000; Pedroty et al., 2005; Stern-Straeter et al., 2005, Serena et al., 2008) and in vivo (DiStefano et al., 2013; Ambrosio et al., 2012) and NMES has been used therapeutically in man to promote the recovery of skeletal muscle from injury (Dirks et al., 2014; Bittar and Cliquet, 2010; Kim et al., 2010; Stackhouse et al., 2007). The present invention uses NMES to promote the successful generation of mature human muscle fibers in mice in vivo.

NMES involves the use of a device which transmits an electrical impulse to the skin over selected muscle groups by way of electrodes. The NMES causes muscles to contract as a form of exercise or physical therapy. NMES of healthy muscle is intended to strengthen or maintain muscle mass during or following periods of enforced inactivity, maintain or gain range of motion, facilitate voluntary muscle control, and temporaily reduce spasticity. Standard treatment in human can be 3 to 4 sessions a week for one month when used as adjunctive therapy or muscle retraining. As a means for enhancing engraftment in a nonhuman animal, such as a mouse, in certain embodiments, NEMS can be administered intermittently from one day to about 28 days or longer from the time of injection of myogenic cells. More specifically, in about 7 days from injection of myogenic cells. This can occur for a period of 4 to 5 weeks. In certain embodiments, NMES can be administered intermittently at 150 Hz for 500 msec, repeated 10 times. This can than be repeated 4 times with 2 minute rests, for a total of 40 repetitions, three times per week, for 4-5 weeks. One of ordinary skill in the art could change frequency, repetition, and timing to suit experimentation.

The TA muscle may be eliminated by any method known in the art, including, but not limited to, irradiating the hindlimb with X-rays and then injecting it with a toxin such as cardiotoxin, $BaCl_2$ or notexin. As a representative example, cardiotoxin CTX may be injected in a dose of 60 µl of a 0.3 mg/ml solution. For example, it is known in the art that the neurotoxin from tiger snake venom (notexin, Notechis scutatus) has a LD50 6.4 mg/kg sc mice, minimum dose for myoglobinuria 1.4 mg/kg sc mice. Other toxins such as P. australis venom are lethal and can cause myoglobinuria in mice, having a LD50 for 0.25 mg/kg ip mice. See Leonardi et al 1979. One of ordinary skill in the art would know how to determine the proper dosage for the toxin of choice (i.e., $BaCl_2$ or notexin) to induce paralysis. Therapeutic electrical stimulation can be applied for the first time from between one day and about 14 days from the time the myogenic cells are injected. In certain embodiments electrical stimulation is begun approximately one week after the myogenic cells are injected. The duration and amount of electrical stimulation may range beyond what is specifically used in the working examples described herein.

Treatment of the Muscle Disease FSHD

Over the last decade several reports examined the possibility that human myoblast therapy is useful for the treatment of genetic muscle diseases. Improved strains of immunodeficient mice have been developed that allow efficient engraftment, differentiation and maturation of human myogenic cells (Huard et al., 1994; Skuk et al., 1999; Pye et al., 2004; Silva-Barbosa et al., 2005; Silva-Barbosa et al., 2008). Earlier studies of grafts formed by injecting human myogenic precursor cells into mice yielded limited numbers of muscle fibers with human myonuclei (Mouly et al., 2005; Mamchaoui et al., 2011; Reed et al., 2007; Riederer et al., 2012).

Two approaches have been tested to develop grafts of human muscle tissues in mice. In one approach, xenografts are created by introducing small pieces of mature human muscle myofibers, obtained at biopsy, and suturing them to muscles in immunodeficient mice (Zhang et al, 2014). Over time, some of these grafts survive and reform mature muscle tissue that is largely human in origin. But these grafts are fibrotic and can also contain significant numbers of murine myonuclei. Although the mice carrying these human grafts provide potentially excellent models, it would be difficult to generate in the numbers needed for therapeutic testing.

As an alternative approach, the ability of human myogenic cells to develop into mature human muscle tissue in immunodeficient or dystrophic mice has been investigated. (Riederer et al., 2012; Silva-Barbosa et al., 2008; Silva-Barbosa et al., 2005). In these studies, the endogenous murine muscle is typically eliminated by freezing or injection of a toxin, and, in some cases, regeneration is reduced by prior X-irradiation. Human myoblasts are often tagged with an enzyme such as luciferase (Laumonier et al., 2013; Libani et al., 2011), or a fluorescent protein such as green fluorescent protein (GFP) (Benabdallah et al., 2013; Quenneville et al., 2007), to enable them to be tracked by luminometric or fluorescence methods after they are injected into adult mouse skeletal muscle. After injection, mice have been exposed to different pharmacological agents, such as Losartan (Fakhfakh et al., 2012b), to alter angiotensin II signaling, and a soluble form of the receptor for myostatin, ActRIIB-Fc (Fakhfakh et al., 212a), to promote myogenesis and reduce fibrosis.

These treatments have improved the survival of the engrafted human myogenic cells in mice and their differentiation into myofibers. However, the muscles they form are very small and therefore difficult to study by physiological morphological and genomic methods. The engrafted muscle grafts may also contain a large number of murine myonuclei, indicating that they are largely hybrid in nature (Fakhfakh et al., 2012a; Ehrhardt et al., 2007).

In addition, the methods that have been used to suppress murine myogenesis following injury to murine muscle proved ineffective in preventing murine muscle from reforming. As the engrafted cells must compete with myogenic precursor cells derived from murine satellite cells, they can at best form myofibers of mixed human-mouse origin. This is less than optimal for studying the human dystrophic phenotype, considering the likelihood of genetic complementation compensating for the cause of the myopathy in hybrid fibers.

Studies of the pathogenic mechanisms underlying muscular dystrophies often require animal models, but models of some human muscle diseases are not yet available. Of specific interest in certain embodiments is FSHD. FSHD is one of the most common forms of muscular dystrophy in adults, caused by an epigenetic derepression of the macrosatellite repeat D4Z4 in the 4q35 region, either by contraction of the repeat array (FSHD1; Wijmenga et al., 1992; vanDeutekom et al., 1993) or by mutations in modifier genes, such as SMCHD1 (FSHD2) (Lemmers et al., 2012). These genetic and epigenetic changes combined with FSHD-permissive chromosomal alleles (Lemmers et al., 2010) can lead to an ectopic expression of the DUX4 retrogene, a potent germline transcription factor, residing in each D4Z4 repeat.

Although accumulating evidence supports the possible pathogenic role of DUX4 in FSHD development, DUX4 may not be the sole candidate gene. A recent model proposes that deregulation of a global transcriptional cascade involving numerous DUX4 target genes, initially triggered by DUX4 activation randomly in rare FSHD myonuclei, could lead to muscle atrophy, inflammation, oxidative stress and defects in differentiation process, all key features of FSHD (Tassin et al., 2012). Pathogenesis in FSHD may also be linked to other gene products, including long noncoding RNAs (Cabianca et al., Cell. 2012; PMID: 22541069) and miRNAs (Cheli et al., PLoS One. 2011; PMID: 21695143). Despite extensive study, the molecular mechanisms underlying FSHD are still not fully understood.

As a result, a valid mouse model of the disease was in need of development. Without one, studies of the disease in vivo are significantly limited. Several laboratories have generated mice by transgenic or viral expression of DUX4 (Krom et al., 2012; Wallace et al., 2011), or potential downstream mediators of their activity, such as PITX1 (Dixit et al., 2007) and CRYM (Reed et al., 2007; our unpublished data). None have so far reproduced the phenotype seen in biopsies of FSHD patients. Indeed, the likelihood that FSHD is caused by both genetic and epigenetic changes (Jones et al., 2012; Lemmers et al., 2012; Lemmers et al., 2010; Rahimov et al., 2012), regulated by modifier genes that remain to be identified (Jones et al., 2012), casts doubt on the possibility that a simple transgenic model can be created by manipulating individual genes.

In certain aspects of the invention, a murine model for FSHD should reproduce all the features of FSHD muscle, retaining the morphological, physiological and genomic differences found in fresh biopsies. As the mechanisms underlying pathogenesis in FSHD are still unclear, it is necessary to construct muscle tissue for study in vivo from patient-derived human myogenic cells, which presumably retain these disease-causing changes. Applicant optimized transplantation conditions for successful engraftment of a cell line derived from a FSHD patient using immortalized human myogenic precursor cells and injecting these myoblast cells into the tibialis anterior (TA) muscle compartment in the anterior hindlimb of immunodeficient NOD-Rag1$^{null}$ IL2ry$^{null}$ mice (NOD-Rag).

In one embodiment, hMPCs from a patient with Facioscapulohumeral muscular dystrophy were introduced into mice, following the methods described herein, including NMES, muscle fibers of human origin developed and expressed several genes typical of FSHD tissue. In particular, the fibers generated following engraftment of these cells labeled with antibodies to human β-spectrin and to human lamin A/C (not shown). Furthermore, when harvested and assayed by quantitative RT-PCR methods and compared to the grafts formed by LHCN cells, they contained several fold higher levels of mRNA encoding DUX4 (not shown), a protein believed to be involved in the pathogenesis of FSHD. Consistent with this, quantitative RT-PCR methods also showed significant increases in mRNAs encoding at least two gene products that are transcribed when DUX4 is elevated (not shown). These results indicate that our methods are not limited to LHCN cells, that they are generally applicable to hMPCs, including hMPCs derived from subjects with neuromuscular disease, and that the grafts that they produce retain many of the characteristics of the tissue from which the hMPCs originated.

The usefulness of certain embodiments was also tested by creating xenografts of hMPCs from diseased tissue in mimicking the disease phenotype in mice. Immortalized hMPCs from a patient with FSHD were used for this purpose. These cells, like LHCN cells, had been transduced to express firefly luciferase. Using the methods described, it was found that FSHD cells engrafted in mice at least as well as in controls. PCR for DUX4 was performed on mRNA from 2 grafts (G31M3, P19M2), and 2 mouse TA muscles. 17ABic was a positive control for Dux4. hRPL13A was a human-specific marker. The grafts formed from FSHD hMPCs express Dux4 but the controls do not (data not shown). qPCR for two Dux4 downstream genes was performed on mRNA from 1 graft formed by LHCN cells and 2 by FSHD cells The results show a significant increase (p<0.05) in expression of TRIM43 and ZSCAN4 in grafts formed by the FSHD hMPCs (data not shown). Therefore, xenografts formed by FSHD hMPCs preserve the distinct genetic program observed in the hMPCs in culture and in the biopsies from which those cells were originally derived. With further optimization, certain embodiments will yield mice carrying mature FSHD muscles. The mice carrying these grafts should be suitable for testing therapies to treat FSHD. The most sensitive and reliable assays utilize qRT-PCR of FSHD-specific biomarkers, which are applicable to Applicant's mouse model. A therapeutic drug for FSHD should bring biomarker levels to close to controls. Thus, the methods described here should make it possible to screen compounds and compare therapeutic efficacies of different drugs on living FSHD muscle tissue in vivo.

In certain embodiments, optimization of these unique xenografting conditions for successful transplantation of normal immortalized human myoblasts in mice will allow future testing of similar immortalized cell lines derived from FSHD patients and their first-degree relatives (Mamchaoui et al., 2011; Stadler et al., 2011). It is expected that the mature myofibers derived from immortalized FSHD myoblasts will show the phenotype of FSHD muscle, with all the associated genetic, epigenetic, physiological and morphological properties (Geng et al., 2012; Jones et al., 2012; Lassche et al., 2013; Lemmers et al., 2010; Rahimov et al., 2012; Reed et al., 2006), independently of any particular molecular model of pathogenesis.

Considering the feasibility of assaying this mature human muscle tissue in mice morphologically and physiologically, and the validity and use of LHCN immortalized normal cells as a universal human cellular model, other embodiments are directed to the application of such a xenotransplant model to not only FSHD, but a wide variety of neuromuscular disorders.

Methods for Producing a Non-Human Model for Human Muscle Disease

The invention further provides a method for producing a non-human animal that models a human muscular disease. A non-human animal such as an immunocompromised mouse suitable for xenografting is obtained. The hindlimb of the non-human animal is irradiated with X-rays. The TA muscle is extracted and a cardiotoxin or other toxin (e.g., BaCl$_2$ or notexin) is injected along the length of the TA muscle to induce degeneration of myofibers of the TA muscle in the non-human animal thereby and creating a volume or compartment where TA muscle used to be located. HMPCs or LHCN cells obtained from a human muscular disease are tagged with an enzyme such as luciferase and injected into the non-human TA muscle compartment to form a graft. The peroneal nerve of the injected hindlimb is subjected to electrical stimulation. Contractile function of myofibers of human origin is then assessed. The graft generated by human myogenic precursor cells obtained from a human muscular disease may then be compared with cells obtained from a non-diseased muscle and ultimately screened for therapeutic drugs. Non-human animal models generated by this method are also contemplated.

In some embodiments where hMPCs are implanted into an animal subject, the animal can be used as an in vivo humanized model of muscular disease. For example, an animal model which comprises functional, innervated, vascularized human muscle tissue, can be used to screen for therapeutic agents, viruses or drugs which affect any one, or a combination of viability, functionality, contractibility, differentiation of the human muscle tissue.

Accordingly, one embodiment relates to the use of an in vivo humanized model of muscle disease as an assay, for example to assess drug toxicity (e.g. myotoxicity) on human muscle tissue in vivo (e.g. to identify agents which increase apoptosis, decrease viability, modulate (e.g. increase or decrease by a statistically significantly amount) contractibility and/or conductivity of muscle tissue). In some embodiments, the drugs and/or compounds can be existing drugs or compounds, and in other embodiments, the drugs or compounds can be new or modified drugs and compounds.

Any suitable immunodeficient animal can be used for implanting a population of hMPC cells to generate an in vivo humanized model of muscle disease as disclosed herein, (such as NRG mice, NOD-Rag mice, nude mice, such as SCID mice, or animals rendered immunodeficient chemically or by irradiation) The human muscle tissues can be harvested after a period of growth, and assessed as to whether the human muscle tissue is still present, viable and functioning normally.

In some embodiments, the LHCN cells or hMPCs of other origin administered to the subject can be transduced with retrovirus to express a detectable label such as luciferase constitutively, to facilitate in vivo imaging after engraftment. Others can express a detectable label (such as green fluorescent protein, or beta-galactosidase); alternatively, they may have been prelabeled (for example, with BrdU or $^{3H}$thymidine), or they may be detected by virtue of their expression of a constitutive cell marker (for example, using human-specific antibody). The presence and phenotype of the administered LHCN cells can be assessed several methods, including but not limited to luminometry, immunohistochemistry, or RT-PCR analysis using primers and hybridization conditions that cause amplification to be specific for human polynucleotides, according to published sequence data.

The effect of an agent administered to an in vivo humanized model of muscle disease can be assessed by many methods, including but not limited to improvement in muscle histology, improvement in contractile function, reduction of fibrosis or fatty infiltrates, reduction in the expression of disease-specific markers, increased expression of muscle specific proteins or mRNAs, or improved recuperation following intentional injury to the humanized muscle tissue.

In such an embodiment, the in vivo humanized model of muscle disease of the invention can be used to screen for agents which alleviate the injury. In alternative embodiments, the in vivo humanized model of muscle disease can be assessed by the degree of muscle recuperation that ensues from inflicting injury to the human muscle tissue. The manner in which human muscle tissue responds to an agent, particularly a pharmacologic agent, including the timing of responses, is an important reflection of the physiologic state of the human muscle tissue.

The use of the in vivo humanized model of muscle disease as disclosed herein provides significant advantages over existing methods to assess agents on muscle tissue, because the in vivo humanized model of muscle disease comprises human muscle tissue which is formed from e.g., LHCNs or hMSCs in vivo, and is properly re-vascularized and comprises all the desired cell types of muscle tissue, including cells of myocyte phenotypes, as well as characteristics and properties of functional muscle tissue. This is highly advantageous as it provides a model of human muscle tissue in vivo, which is significantly advantageous over existing muscle function assays which either are assays using human muscle tissue in vitro, or are in vivo models using non-human muscle tissue.

In some embodiments, an agent administered to an in vivo humanized model of muscle disease as disclosed herein can be selected from a group of a chemical, small molecule, chemical entity, nucleic acid sequences, nucleic acid analogues or protein or polypeptide or analogue of fragment thereof. In some embodiments, the nucleic acid is DNA or RNA, and nucleic acid analogues, for example can be peptide nucleic acid "PNA", pseudo-complementary peptide nucleic acids, "pcPNA" and locked nucleic acids, "LNA". A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

In some embodiments, at least one agent is administered to an in vivo humanized model of muscle disease as disclosed herein by any suitable means known to one of ordinary skill in the art. In some embodiments, administration occurs more than once, for example at multiple different time points. In some embodiments, the administration of an agent to an in vivo humanized model of muscle disease is continuous, for example via means of an infusion pump or catheter or the like, or via a slow-release formulation of the agent. In some embodiments, the agent is administered locally to the site of the human muscle tissue in the in vivo humanized model of muscle disease, or alternatively, systemically to the in vivo humanized model of muscle disease.

In some embodiments, an agent is administered to an in vivo humanized model of muscle disease via any or a combination of the following administration methods; systemic administration, intravenous, transdermal, intrasynovial, intramuscular, oral administration, parenteral administration, intraarterial administration, intrathecal administration, intraventricular administration, intraparenchymal, intracranial, intracisternal, intrastriatal, and intranigral administration, and intracoronary administration.

In some embodiments, the agents are conveniently administered to the an in vivo humanized model of muscle disease in a pharmacological applicable carrier, such as solution, or readily soluble form. The agents may be added in a pump (e.g. flow-through system), as a stream, intermittent or continuous, or alternatively, adding a bolus of the compound, singly or incrementally, to an otherwise static solution. In some embodiments, agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

In some embodiments, an agent may be applied to the media comprising the LHCN cells or hMPCs prior to the implantation into the subject, where the agent contacts the LHCN cells and induces its effects. Alternatively, the agent may be intracellular within the LHCN cells as a result of introduction of the nucleic acid sequence into the cell and its transcription resulting in the production of the nucleic acid and/or protein agent within the cell.

In some embodiments, an agent also encompasses any action and/or event the in vivo humanized model of muscle disease as disclosed herein is are subjected to. As a non-limiting example, an action can comprise any action that triggers a physiological change in human muscle tissue in the in vivo humanized model of neuromuscular disease as disclosed herein, for example but not limited to; heat-shock, ionizing irradiation, cold-shock, electrical impulse, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli defined below. The exposure to agent may be continuous or non-continuous.

Methods for Determining Myotropism of Viruses for Gene Therapy

In other embodiments, the mice carrying the grafts formed by LHCN cells have potentially broad uses, e.g., determining the myotropism of viruses for gene therapy, assessing the effects of drugs, antibodies, microorganisms and toxins on mature human muscle, and developing new approaches to treating a number of human diseases of muscle. Specifically applied to muscular dystrophies such as FSHD, the methods are significant because they provide an excellent means of generating mature FSHD muscle tissue in mice, leading to a valuable tool for the study of pathology of the disease and its treatment, including the possible use of autologous myoblast-based therapies.

For purposes of the present invention, gene therapy refers to the transfer and stable insertion of new genetic information into cells for the therapeutic treatment of muscle diseases or muscle disorders. A foreign sequence or gene is transferred into hMPCs that proliferate to spread the new sequence or gene throughout the cell population. Known methods of gene transfer include microinjection, electroporation, liposomes, chromosome transfer, transfection techniques, calcium-precipitation transfection techniques, and the like. For example, muscular dystrophy may result from a loss of gene function, as a result of a mutation for example, or a gain of gene function, as a result of an extra copy of a gene, such as three copies of a wild-type gene, or a gene over expressed as a result of a mutation in a promoter, for example. Expression may be altered by activating or deactivating regulatory elements, such as a promoter. A mutation may be corrected by replacing the mutated sequence with a wild-type sequence or inserting an antisense sequence to bind to an over expressed sequence or to a regulatory sequence.

Numerous techniques are known in the art for the introduction of foreign genes into cells and may be used to construct the recombinant cells for purposes of gene therapy, in accordance with this embodiment of the invention. The technique used should provide for the stable transfer of the heterologous gene sequence to the precursor cell, so that the heterologous gene sequence is heritable and expressible by stem cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, M. J., 1985, Pharmac. Ther. 29:69-92, incorporated herein by reference in its entirety). These methods may be extended to precursor cells transfected with plasmid constructs that encode a secreted protein, allowing the grafts that are generated to provide systemic benefit to the subject, e.g., replacement of defective or absent polypeptide hormone, and serum factors.

In other embodiments, muscle tissue with hereditary muscle disease may be identified. hMPCs obtained from this muscle tissue may be isolated. It is possible to then insert a gene into these hMPCs, using conventional molecular biology techniques known to those in the art, to replace a gene that is mutated or missing, while maintaining exactly the same genetic background. The hMPCs expressing the healthy gene may be injected into a subject in need of muscle repair. Ultimately, the muscle in which the genetic defect is so corrected can reform.

Pharmaceutical Compositions and Kits Comprising them

In certain embodiments, pharmaceutical compositions comprising cells and/or different drugs, different hormones or other biologically active compounds may be used to promote engraftment or to optimize generation of new muscle tissue. Such reagents may include, but are not limited to, losartan, IGF1, antibodies to TFG-β proteins, and the region of the ActRIIB receptor that binds proteins of the TGF-β superfamily. In other embodiments, kits comprising the pharmaceutical composition may prevent rejection of the graft. The pharmaceutical composition and kit comprising it may be useful for repairing wounded or injured muscle, in addition to diseased muscle. For example, the methods may be applicable to treating subjects with hMPCs derived from their own healthy muscles in order to replace muscle tissue lost to wounds (e.g., injury due to military combat).

In some embodiments, the present invention relates to a pharmaceutical composition and kits comprising them comprising the myoblast cells capable of forming muscle tissue as disclosed herein. The pharmaceutical compositions may further comprise a pharmaceutically acceptable carrier. The myoblast composition can be administered to a subject alone or in combination with other cells, tissue, matrix components, tissue fragments, or growth factors as disclosed herein. In alternative embodiments, other known growth factors can be administered in combination with the myoblast cells, e.g., resorbable plastic scaffolds, or other additive intended to enhance the delivery, efficacy, tolerability, vascularization, or function of the implanted myoblast cell population.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention.

REFERENCES

[1] Mamchaoui K, Trollet C, Bigot A, Negroni E, Chaouch S, et al (2011). Immortalized pathological human myoblasts: towards a universal tool for the study of neuromuscular disorders. Skeletal Muscle; 1:34.

[2] Stadler G, Chen J C, Wagner K, Robin J D, Shay J W, Emerson C P Jr, Wright W E (2011). Establishment of clonal myogenic cell lines from severely affected dystrophic muscles—CDK4 maintains the myogenic population. Skelet Muscle; 1:12.

[3] Partridge T A (2013). The mdx mouse model as a surrogate for Duchene muscular dystrophy. FEBS J; 280:4177-4186.

[4] Kobayashi K, Izawa T, Kuwamura M, Yamate J (2012). Dysferlin and animal models for dysferlinopathy. J Toxicol Pathol; 25:135-147.

[5] Quattrocelli M, Cassano M, Crippa S, Perini I, Sampaolesi M (2010). Cell therapy strategies and improvements for muscular dystrophy. Cell Death Differ; 17:1222-1229.

[6] Vainzof M, Ayub-Guerrieri D, Onofre P C, Martins P C, Lopes V F, Zilberztajn D, et al (2008). Animal models for genetic neuromuscular diseases. J Mol Neurosci; 3:241-248.

[7] Zhang Y, King O D, Rahimov F, Jones T I, Ward C W, Kerr J P, et al (2014). Human skeletal muscle xenograft as a new preclinical model for muscle disorders. Hum Mol Genet; 23:3180-3188.

[8] Riederer I, Negroni E, Bencze M, Wolff A, Aamiri A, Di Santo J P, et al (2012). Slowing down differentiation of engrafted human myoblasts into immunodeficient mice correlates with increased proliferation and migration. Mol Ther; 20:146-154.

[9] Silva-Barbosa S D, Butler-Browne G S, de Mello W, Riederer I, Di Santo J P, Savino W, et al (2008). Human myoblast engraftment is improved in laminin-enriched microenvironment. Transplantation; 85:566-575.

[10] Silva-Barbosa S D, Butler-Browne G S, Di Santo J P, Mouly V (2005). Comparative analysis of genetically engineered immunodeficient mouse strains as recipients for human myoblast transplantation. Cell Transplant; 14:457-467.

[11] Laumonier T, Pradier A, Hoffmeyer P, Kindler V, Menetrey J (2013). Low molecular weight dextran sulfate binds to human myoblasts and improves their survival after transplantation in mice. Cell Transplant; 22:1213-1226.

[12] Libani I V, Lucignani G, Gianelli U, Degrassi A, Russo M, Bosari S, et al (2012). Labeling protocols for in vivo tracking of human skeletal muscle cells (HSkMCs) by magnetic resonance and bioluminescence imaging. Mol Imaging Biol; 14:47-59.

[13] Benabdallah B F, Duval A, Rousseau J, Chapdelaine P, Holmes M C, Haddad E, et al (2013). Targeted gene addition of microdystrophin in mice skeletal muscle via human myoblast transplantation. Mol Ther Nucleic Acids; 2:e68.

[14] Quenneville S P, Chapdelaine P, Skuk D, Paradis M, Goulet M, Rousseau J, et al (2007). Autologous transplantation of muscle precursor cells modified with a lentivirus for muscular dystrophy: human cells and primate models. Mol Ther; 15:431-438.

[15] Fakhfakh R, Lamarre Y, Skuk D, Tremblay J P (2012b). Losartan enhances the success of myoblast transplantation. Cell Transplant; 21:139-152.

[16] Fakhfakh R, Lee S J, Tremblay J P (2012a). Administration of a soluble activin type IIB receptor promotes the transplantation of human myoblasts in dystrophic mice. Cell Transplant; 21:1419-1430.

[17] Ehrhardt J, Brimah K, Adkin C, Partridge T, Morgan J (2007). Human muscle precursor cells give rise to functional satellite cells in vivo. Neuromuscul Disord; 17:631-638.

[18] Serena E, Flaibani M, Carnio S, Boldrin L, Vitiello L, De Coppi P, Elvassore N. Electrophysiologic stimulation improves myogenic potential of muscle precursor cells grown in a 3D collagen scaffold. Neurol Res; 30:207-214.

[19] De Deyne P G (2000). Formation of sarcomeres in developing myotubes: role of mechanical stretch and contractile activation. Am J Physiol Cell Physio; 279:C1801-1811.

[20] Distefano G, Ferrari R J, Weiss C, Deasy B M, Boninger M L, Fitzgerald G K, et al (2013). Neuromuscular electrical stimulation as a method to maximize the beneficial effects of muscle stem cells transplanted into dystrophic skeletal muscle. PLoS One; 8:e54922.

[21] Ambrosio F, Fitzgerald G K, Ferrari R, Distefano G, Carvell G (2012). A murine model of muscle training by neuromuscular electrical stimulation. J Vis Exp; (63): e3914.

[22] Dirks M L, Wall B T, Snijders T, Ottenbros C L, Verdijk L B, and van Loon L J (2014). Neuromuscular electrical stimulation prevents muscle disuse atrophy during leg immobilization in humans. Acta Physiol (Oxf); 210:628-641.

[23] Bittar C K, and Cliquet A Jr (2010). Effects of quadriceps and anterior tibial muscles electrical stimulation on the feet and ankles of patients with spinal cord injuries. Spinal Cord; 48(12):881-885.

[24] Kim K M, Croy T, Hertel J, Saliba S (2010). Effects of neuromuscular electrical stimulation after anterior cruciate ligament reconstruction on quadriceps strength, function, and patient-oriented outcomes: a systematic review. J Orthop Sports Phys Ther; 40:383-391.

[25] Stackhouse S K, Binder-Macleod S A, Stackhouse C A, McCarthy J J, Prosser L A, Lee S C (2007). Neuromuscular electrical stimulation versus volitional isometric strength training in children with spastic diplegic cerebral palsy: a preliminary study. Neurorehabil Neural Repair; 21:475-485.

[26] Zhu C H, Mouly V, Cooper R N, Mamchaoui K, Bigot A, Shay J W, et al (2007). Cellular senescence in human myoblasts is overcome by human telomerase reverse transcriptase and cyclin-dependent kinase 4: consequences in aging muscle and therapeutic strategies for muscular dystrophies. Aging Cell; 6:515-523.

[27] Ambrosio F, Ferrari R J, Distefano G, Plassmeyer J M, Carvell G E, Deasy B M, et al (2010). The synergistic effect of treadmill running on stem-cell transplantation to heal injured skeletal muscle. Tissue Eng Part A; 16:839-849.

[28] Bouchentouf M, Benabdallah B F, Mills P, Tremblay J P (2006). Exercise improves the success of myoblast transplantation in mdx mice. Neuromuscul Disord; 16:518-529.

[29] Pearson T, Shultz L D, Miller D, King M, Laning J, Fodor W, et al (2008). Non-obese diabetic-recombination activating gene-1 (NOD-Rag1 null) interleukin (IL)-2 receptor common gamma chain (IL2r gamma null) null mice: a radioresistant model for human lymphohaematopoietic engraftment. Clin Exp Immunol; 154:270-284.

[30] Lovering R M, Roche J A, Bloch R J, De Deyne P G (2007). Recovery of function in skeletal muscle following 2 different contraction-induced injuries. Arch Phys Med Rehabil; 88:617-625.

[31] Roche J A, Lovering R M, Roche R, Ru L W, Reed P W, Bloch R J (2010). Extensive mononuclear infiltration and myogenesis characterize recovery of dysferlin-null skeletal muscle from contraction-induced injuries. Am J Physiol Cell Physiol; 298:C298-312.

[32] Harris J B (2003). Myotoxic phospholipases A2 and the regeneration of skeletal muscles. Toxicon; 42:933-945.

[33] Couteaux R, Mira J C, d'Albis A (1988). Regeneration of muscles after cardiotoxin injury. I. Cytological aspects. Biol Cell; 62(2):171-182.

[34] Briguet A, Courdier-Fruh I, Foster M, Meier T, Magyar J P (2004). Histological parameters for the quantitative assessment of muscular dystrophy in the mdx-mouse. Neuromuscul Disord; 14:675-682.

[35] Riederer I, Negroni E, Bencze M, Wolff A, Aamiri A, Di Santo J P, et al (2012). Slowing down differentiation of engrafted human myoblasts into immunodeficient mice correlates with increased proliferation and migration. Mol Ther; 20:146-154.

[36] Skuk D, Paradis M, Goulet M, Chapdelaine P, Rothstein D M, Tremblay J P (2010). Intramuscular transplantation of human postnatal myoblasts generates functional donor-derived satellite cells. Mol Ther; 18:1689-1697.

[37] Negroni E, Riederer I, Chaouch S, Belicchi M, Razini P, Di Santo J, et al (2009). In vivo myogenic potential of human CD133+ muscle-derived stem cells: a quantitative study. Mol Ther; 17:1771-1778.

[38] Zhou D, Ursitti J A, Bloch R J (1998). Developmental expression of spectrins in rat skeletal muscle. Mol Biol Cell; 9:47-61.

[39] Li Z, Mericskay M, Agbulut O, Butler-Browne G, Carlsson L, Thornell L E, et al (1997). Desmin is essential for the tensile strength and integrity of myofibrils but not for myogenic commitment, differentiation, and fusion of skeletal muscle. J Cell Biol; 139:129-144.

[40] Li Z L and Paulin D (1991). High level desmin expression depends on a muscle-specific enhancer. J Biol Chem; 266:6562-6570.

[41] Hill C S, Duran S, Lin Z X, Weber K and Holtzer H (1986). Titin and myosin, but not desmin, are linked during myofibrillogenesis in postmitotic mononucleated myoblasts. J Cell Biol; 103:2185-2196.

[42] Sharp P S, Bye-a-Jee H, and Wells D J (2011). Physiological characterization of muscle strength with variable levels of dystrophin restoration in mdx mice following local antisense therapy. Mol Ther; 19:165-171.

[43] Lazarides E (1980) Intermediate filaments as mechanical integrators of cellular space. Nature; 283: 249-256.

[44] Lazarides W and Hubbard B D (1976) Immunological characterization of the subunit of the 100 Å filaments from muscle cells. Proc Natl Acad Sci USA; 73: 4344-4348.

[45] Capetanaki Y, Milner D J, and Weitzer G (1997). Desmin in muscle formation and maintenance: knockouts and consequences. Cell Struct Funct.; 22:103-116.

[46] Bader D (1981). Density and distribution of alpha-bungarotoxin-binding sites in postsynaptic structures of regenerated rat skeletal muscle. J Cell Biol; 88:338-345.

[47] Ko P K, Anderson M J, and Cohen M W (1977). Denervated skeletal muscle fibers develop discrete patches of high acetylcholine receptor density. Science; 196:540-542.

[48] Nowack A, Yao J, Custer K L, and Bajjalieh S M (2010). SV2 regulates neurotransmitter release via multiple mechanisms. Am J Physiol Cell Physiol; 299: C960-967.

[49] Vautrin J (2009). SV2 frustrating exocytosis at the semi-diffusor synapse. Synapse; 63: 319-338.

[50] McLoughlin T J, Snyder A R, Brolinson P G, and Pizza F X (2004). Sensory level electrical muscle stimulation: effect on markers of muscle injury. Br J Sports Med; 38:725-729.

[51] Wang W J, Zhu H, Li F, Wan L D, Li H C, and Ding W L (2009). Electrical stimulation promotes motor nerve regeneration selectivity regardless of end-organ connection. J Neurotrauma; 26:641-649.

[52] Pedrotty D M, Koh J, Davis B H, Taylor D A, Wolf P, and Niklason L E (2005). Engineering skeletal myoblasts: roles of three-dimensional culture and electrical stimulation. Am J Physiol Heart Circ Physiol; 288:H1620-1626.

[53] Stern-Straeter J, Bach A D, Stangenberg L, Foerster V T, Horch R E, Stark G B, et al (2005). Impact of electrical stimulation on three-dimensional myoblast cultures—a real-time RT-PCR study. J Cell Mol Med; 9:883-892.

[54] Gerard C, Forest M A, Beauregard G, Skuk D, and Tremblay J P (2012). Fibrin gel improves the survival of transplanted myoblasts. Cell Transplant; 21:127-137.

[55] Cabianca, Cabianca D S, Casa V, Bodega B, Xynos A, Ginelli E, Tanaka Y, Gabellini D. Cell. 2012 May 11; 149(4):819-31. doi: 10.1016/j.cell.2012.03.035. Epub 2012 Apr. 26.

[56] Cheli S, François S, Bodega B, Ferrari F, Tenedini E, Roncaglia E, Ferrari S, Ginelli E, Meneveri R. PLoS One. 2011; 6(6):e20966. doi: 10.1371/journal.pone.0020966. Epub 2011 Jun. 13.

What is claimed is:

1. A method of generating mature human muscle fibers in a non-human animal model comprising:
   a) obtaining an immunocompromised non-human animal suitable for human xenografting;
   b) X-irradiating a limb of the non-human animal to prevent host muscle regeneration;
   c) injecting a myotoxin along a length of the muscle in the irradiated limb to induce degeneration of myofibers of the muscle in the non-human animal thereby creating a muscle compartment;
   d) injecting immortalized human myogenic precursor cells capable of forming human muscle tissue into the muscle compartment of the limb of the non-human animal, and
   e) subjecting a nerve of the injected limb to therapeutic electrical stimulation configured to enhance engraftment of the myogenic precursor cells,
   wherein the enhanced engraftment of human myogenic precursor cells promotes generation of mature human muscle fibers.

2. The method of claim 1, wherein the non-human animal models human muscle disease.

3. The method of claim 2, wherein the human muscle disease is a disease selected from the group consisting of: amyotrophic lateral sclerosis (ALS), Andersen-Tawil Syndrome, Becker Muscular Dystrophy (BMD), Becker Myotonia Congenita, Bethlem Myopathy, Bulbospinal Muscular Atrophy (Spinal-Bulbar Muscular Atrophy), Carnitine Deficiency, Central Core Disease (CCD), Centronuclear Myopathy, Charcot-Marie-Tooth Disease (CMT), Congenital Muscular Dystrophy (CMD), Congenital Myotonic Dystrophy, Dejerine-Sottas Disease (DSD), Dermatomyositis (DM), Distal Muscular Dystrophy (DD), Duchenne Muscular Dystrophy (DMD), Dystrophia Myotonica (Myotonic Muscular Dystrophy), Emery-Dreifuss Muscular Dystrophy (EDMD), Eulenberg Disease (Paramyotonia Congenita), Facioscapulohumeral Muscular Dystrophy (FSH or FSHD), Finnish (Tibial) Distal Myopathy, Fukuyama Congenital Muscular Dystrophy, Glycogenosis Type 2, Glycogenosis Type 5, Glycogenosis Type 7, Glycogenosis Type 9, Gowers-Laing Distal Myopathy, Hauptmann-Thanheuser MD (Emery-Dreifuss Muscular Dystrophy), Hereditary Inclusion-Body Myositis, Hereditary Motor and Sensory Neuropathy (Charcot-Marie-Tooth Disease), Hyperthyroid Myopathy, Hypothyroid Myopathy, Inclusion-Body Myositis (IBM), Inherited Myopathies, Integrin-Deficient Congenital Muscular Dystrophy, Kennedy Disease (Spinal-Bulbar Muscular Atrophy), Kugelberg-Welander Disease (Spinal Muscular Atrophy), Lactate Dehydrogenase Deficiency, Lambert-Eaton Myasthenic Syndrome (LEMS), Limb-Girdle Muscular Dystrophies (LGMDs), Lou Gehrig's Disease (Amyotrophic Lateral Sclerosis), McArdle Disease (Phosphorylase Deficiency), Merosin-Deficient Congenital Muscular Dystrophy, Metabolic Diseases of Muscle, Mitochondrial Myopathy, Miyoshi Distal Myopathy, Motor Neurone Disease, Muscle-Eye-Brain Disease, Myasthenia Gravis (MG), Myofibrillar Myopathy, Myotonic Muscular Dystrophy (MMD), Myotubular Myopathy (MTM or MM), Nemaline Myopathy, Nonaka Distal Myopathy, Oculopharyngeal Muscular Dystrophy (OPMD), Paramyotonia Congenita, Periodic Paralysis, Peroneal Muscular Atrophy (Charcot-Marie-Tooth Disease), Pompe Disease (Acid Maltase Deficiency), Progressive External Ophthalmoplegia (PEO), Rod Body Disease (Nemaline Myopathy), Spinal Muscular Atrophy (SMA), Spinal-Bulbar Muscular Atrophy (SBMA), Steinert Disease (Myotonic Muscular Dystrophy), Thomsen Disease (Myotonia Congenita), Ullrich Congenital Muscular Dystrophy, Walker-Warburg Syndrome (Congenital Muscular Dystrophy), Welander Distal Myopathy, Werdnig-Hoffmann Disease (Spinal Muscular Atrophy), and ZASP-Related Myopathy.

4. The method of claim 3, wherein the human muscle disease is Facioscapulohumeral Muscular Dystrophy (FSH or FSHD).

5. The method of claim 1, wherein the muscle is a tibialis anterior muscle and optionally is irradiated with X-ray and then the limb is injected with a toxin.

6. The method of claim 1, wherein the non-human animal is a mouse.

7. The method of claim 6, wherein the mouse is an immunocompromised mouse.

8. The method of claim 1, wherein engraftment is promoted by a means other than therapeutic electrical stimulation.

9. The method of claim 8, wherein engraftment is promoted by exercise.

10. The method of claim 1, further comprising:
f) comparing a graft generated by the engraftment of the human myogenic precursor cells obtained from a subject having a human muscular disease with muscle cells obtained from a non-diseased muscle; and
g) screening the graft with therapeutic agents for determination of myotoxicity.

11. The method of claim 10, wherein the non-human animal is a mouse.

12. The method of claim 1, wherein the immunocompromised mouse is strain NOD.Cg-Rag1tm1MomIl24gtm1-Wjl/SZJ (NRG).

13. The method of claim 1, wherein the myotoxin is selected from the group consisting of cardiotoxin from *Naja mossambica mossambica*, BaCl2, and notexin.

14. The method of claim 1, wherein the therapeutic electrical stimulation is intermittent neuromuscular electrical stimulation.

15. The method of claim 14, wherein the therapeutic intermittent neuromuscular electrical stimulation is repeated for a period of 4 to 5 weeks.

16. The method of claim 1, wherein therapeutic electrical stimulation is applied from one day to about 28 days or longer from the time of injection of myogenic cells.

17. The method of claim 16, wherein the therapeutic electrical stimulation is applied about 7 days from injection of myogenic cells.

18. A non-human animal model generated by the method of claim 1.

* * * * *